(12) United States Patent
Kammerer et al.

(10) Patent No.: US 7,226,407 B2
(45) Date of Patent: *Jun. 5, 2007

(54) SURGICAL INSTRUMENT AND METHOD FOR TREATING FEMALE URINARY INCONTINENCE

(75) Inventors: Gene W. Kammerer, East Brunswick, NJ (US); Hans-Jochen Hoepffner, Belle Mead, NJ (US); Susanne Landgrebe, Sulfeld (DE); Brian Luscombe, Branchburg, NJ (US)

(73) Assignee: Ethicon, Inc., Somerville, NJ (US)

( * ) Notice: Subject to any disclaimer, the term of this patent is extended or adjusted under 35 U.S.C. 154(b) by 491 days.

This patent is subject to a terminal disclaimer.

(21) Appl. No.: 10/191,572

(22) Filed: Jul. 9, 2002

(65) Prior Publication Data

US 2002/0188169 A1    Dec. 12, 2002

Related U.S. Application Data

(63) Continuation of application No. 09/873,571, filed on Jun. 4, 2001, now Pat. No. 7,121,997, which is a continuation-in-part of application No. 09/521,801, filed on Mar. 9, 2000, now Pat. No. 6,273,852.

(60) Provisional application No. 60/138,231, filed on Jun. 9, 1999.

(51) Int. Cl.
*A61F 2/00* (2006.01)

(52) U.S. Cl. .......................................... 600/30; 600/37

(58) Field of Classification Search ............ 600/29–31, 600/37; 606/119, 148, 222–225; 128/DIG. 25
See application file for complete search history.

(56) References Cited

U.S. PATENT DOCUMENTS

| | | | |
|---|---|---|---|
| 3,182,662 A | 5/1965 | Shirodkar | |
| 3,212,502 A | 10/1965 | Myers | |
| 3,311,110 A | 3/1967 | Singerman | |
| 3,372,695 A | 3/1968 | Beliveau et al. | |
| 3,472,232 A | 10/1969 | Earl | |
| 3,608,095 A | 9/1971 | Barry | |
| 3,763,860 A | 10/1973 | Clarke | |
| 3,858,783 A | 1/1975 | Kapitanov et al. | |

(Continued)

FOREIGN PATENT DOCUMENTS

AU    278089 B    6/1965

(Continued)

OTHER PUBLICATIONS

Staskin et al; The Gore-tex sling procedure for female sphincteric incontinence: indications, technique, and results 1997; World J Urol; 15:295-299.*

(Continued)

*Primary Examiner*—John P. Lacyk

(57) ABSTRACT

Described is a surgical instrument and method for treating female urinary stress incontinence. The instrument includes a first curved needle-like element defining in part a curved shaft having a distal end and a proximal, a mesh for implanting into the lower abdomen of a female to provide support to the urethra; a second curved needle element having a proximal end and a distal end, and a coupler for simultaneous attachment to the distal end of the first needle and the distal end of the second needle.

14 Claims, 36 Drawing Sheets

U.S. PATENT DOCUMENTS

| | | | |
|---|---|---|---|
| 3,924,633 | A | 12/1975 | Cook et al. |
| 4,037,603 | A | 7/1977 | Wendorff |
| 4,128,100 | A | 12/1978 | Wendorff |
| 4,235,238 | A | 11/1980 | Ogiu et al. |
| 4,392,495 | A | 7/1983 | Bayers |
| 4,441,497 | A | 4/1984 | Paudler |
| 4,509,516 | A | 4/1985 | Richmond |
| 4,549,545 | A | 10/1985 | Levy |
| 4,946,467 | A | 8/1990 | Ohi et al. |
| 5,013,292 | A | 5/1991 | Lemay |
| 5,032,508 | A | 7/1991 | Naughton et al. |
| 5,080,667 | A | 1/1992 | Chen et al. |
| 5,112,344 | A | 5/1992 | Petros |
| 5,180,385 | A | 1/1993 | Sontag |
| 5,250,033 | A | 10/1993 | Evans et al. |
| 5,281,237 | A | 1/1994 | Gimpelson |
| 5,337,736 | A | 8/1994 | Reddy |
| 5,362,294 | A | 11/1994 | Seitzinger |
| 5,368,595 | A | 11/1994 | Lewis |
| 5,368,756 | A | 11/1994 | Vogel et al. |
| 5,382,257 | A | 1/1995 | Lewis et al. |
| 5,383,904 | A | 1/1995 | Totakura et al. |
| 5,403,328 | A | 4/1995 | Shallman |
| 5,441,508 | A | 8/1995 | Gazielly et al. |
| 5,450,860 | A | 9/1995 | O'Conner |
| 5,507,796 | A | 4/1996 | Hasson |
| 5,582,188 | A | 12/1996 | Benderev et al. |
| 5,611,515 | A | 3/1997 | Benderev et al. |
| 5,628,756 | A | 5/1997 | Barker, Jr. et al. |
| 5,645,568 | A | 7/1997 | Chervitz et al. |
| 5,741,299 | A | 4/1998 | Rudt |
| 5,816,258 | A | 10/1998 | Jervis |
| 5,836,315 | A | 11/1998 | Benderev et al. |
| 5,840,011 | A | 11/1998 | Landgrebe et al. |
| 5,855,549 | A | 1/1999 | Newman |
| 5,860,425 | A | 1/1999 | Benderev et al. |
| 5,899,909 | A | 5/1999 | Claren et al. |
| 5,899,999 | A | 5/1999 | De Bonet |
| 5,934,283 | A | 8/1999 | Willem et al. |
| 5,935,122 | A | 8/1999 | Fourkas et al. |
| 5,945,122 | A | 8/1999 | Abra et al. |
| 5,997,554 | A | 12/1999 | Thompson |
| 6,010,447 | A | 1/2000 | Kardjian |
| 6,030,393 | A | 2/2000 | Corlew |
| 6,042,534 | A | 3/2000 | Gellman et al. |
| 6,050,937 | A | 4/2000 | Benderev |
| 6,110,101 | A | 8/2000 | Tihon et al. |
| 6,117,067 | A | 9/2000 | Gil-Vernet |
| 6,221,005 | B1 | 4/2001 | Bruckner et al. |
| 6,273,852 | B1 | 8/2001 | Lehe et al. |
| 6,306,079 | B1 | 10/2001 | Trabucco |
| 6,334,446 | B1 | 1/2002 | Beyar |
| 6,382,214 | B1 | 5/2002 | Raz et al. |
| 6,406,423 | B1 | 6/2002 | Scetbon |
| 6,475,139 | B1 | 11/2002 | Miller |
| 6,491,703 | B1 | 12/2002 | Ulmsten |
| 6,605,097 | B1 | 8/2003 | Lehe et al. |
| 6,612,977 | B2 | 9/2003 | Staskin et al. |
| 6,691,711 | B2 | 2/2004 | Raz et al. |
| 2001/0018549 | A1 | 8/2001 | Scetbon |
| 2001/0049467 | A1 | 12/2001 | Lehe et al. |
| 2002/0028980 | A1 | 3/2002 | Thierfelder et al. |
| 2002/0058959 | A1 | 5/2002 | Gellman |
| 2002/0077526 | A1 | 6/2002 | Kammerer et al. |
| 2002/0091373 | A1 | 7/2002 | Berger |
| 2002/0188169 | A1 | 12/2002 | Kammerer et al. |
| 2003/0004395 | A1 | 1/2003 | Therin |
| 2003/0023138 | A1 | 1/2003 | Luscombe |
| 2003/0149440 | A1 | 8/2003 | Kammerer et al. |
| 2003/0176762 | A1 | 9/2003 | Kammerer |
| 2003/0195386 | A1 | 10/2003 | Thierfelder et al. |
| 2003/0220538 | A1 | 11/2003 | Jacquetin |
| 2004/0039453 | A1 | 2/2004 | Anderson et al. |

FOREIGN PATENT DOCUMENTS

| | | |
|---|---|---|
| AU | 441561 B | 1/1972 |
| DE | 3223153 C1 | 8/1983 |
| DE | 42 20 283 A1 | 12/1993 |
| DE | 4334419 A1 | 4/1995 |
| EP | 0 598 976 A2 | 6/1994 |
| EP | 0 668 056 A1 | 8/1995 |
| EP | 0 774 240 A1 | 5/1997 |
| EP | 0941712 A1 | 9/1999 |
| EP | 1025811 A | 8/2000 |
| GB | 378288 A | 8/1932 |
| NL | 1001251 C | 3/1997 |
| SE | 503271 C2 | 4/1996 |
| WO | WO 90/03766 A1 | 4/1990 |
| WO | WO 96/06567 A1 | 3/1996 |
| WO | WO 96/06597 | 3/1996 |
| WO | WO 97/13465 | 4/1997 |
| WO | WO 98/31301 A1 | 7/1998 |
| WO | WO 98/35632 A1 | 8/1998 |
| WO | WO 99/16381 A1 | 4/1999 |
| WO | WO 01/06951 A1 | 2/2001 |
| WO | WO 02/28312 A1 | 4/2002 |
| WO | WO 02/38079 | 5/2002 |
| WO | WO 02/058564 A2 | 8/2002 |
| WO | WO 2004/012626 A1 | 2/2004 |

OTHER PUBLICATIONS

Norris et al; Use of Synthetic Material in Sling Surgery: A Minimally Invasive Approach; Jun. 1996; Journal of Endourology; vol. 10, No. 3 227-230.*

O'Donnell; Combined Raz Urthral Suspension and McGuire Pubovagina Sling For Treatment of Complicated Stress Urinary Incontinence; Jan. 1992; Arkansas Med. Soc.; vol. 88, No. 8, pp. 389-392.*

Petros, P.E. Papa, "Vault Prolapse II: Restoration of Dynamic Vaginal Supports by Infracoccygeal Sacropexy, an Axial Day-Case Vaginal Procedure", International Urogynecol Journal (2001) vol. 12, pp. 296-303, Springer-Verlag London Ltd.

Petros, P.E. Papa, Vault Prolapse I: "Dynamic Supports of the Vagina", International Urogynecol Journal (2001) vol. 12, pp. 292-295, Springer-Verlag London Ltd.

PCT International Search Report PCT/US03/04181 dated Jul. 8, 2003.

"AMS Sparc™ Sling System", American Medical Systems, Inc., Minnetonka, MN, 2001, pp. 1-7.

"TVT Tension-free Vaginal Tape, Minimally Invasive Highly Effective Treatment for Female Stress Urinary Incontinence", Gynecare, Ethicon, Inc., 1999, pp. 1-6.

Giberti, "Transvaginal Sacrospinous Colpopexy by Palpation-A New Minimally Invasive Procedure Using an Anchoring System", Urology vol. 57 (2001) pp. 666-669.

Cosson et al, "Cystocele Repair by Vaginal Patch", Progress en Urologie vol. 11 (2001) pp. 340-346.

Collinet et al, "The Vaginal Patch for Vaginal Cure of Cystocele", J. Gynecol. Obstet. Biol. Reprod. vol. 29, No. 2 (2000) pp. 197-201.

Leanza et al, "New Technique for Correcting Both Incontinence and Cystocele: T.I.C.T.", Urogynaecologia International Journal vol. 15, No. 3 (2001) pp. 133-140.

EPO Supplementary Search Report dated Aug. 2, 2004, for corresponding EP application 02776559.3.

Supplementary Partial European Search Report dated Sep. 23, 2004, for corresponding EP application 00928947.1.

U.S. Appl. No. 09/716,546, Ethicon, Inc.

EP communication dated Sep. 13, 2005, for corresponding EP application 00928947.1.

EP Search Report dated Sep. 14, 2005, for corresponding EP application 04078476.1.

* cited by examiner

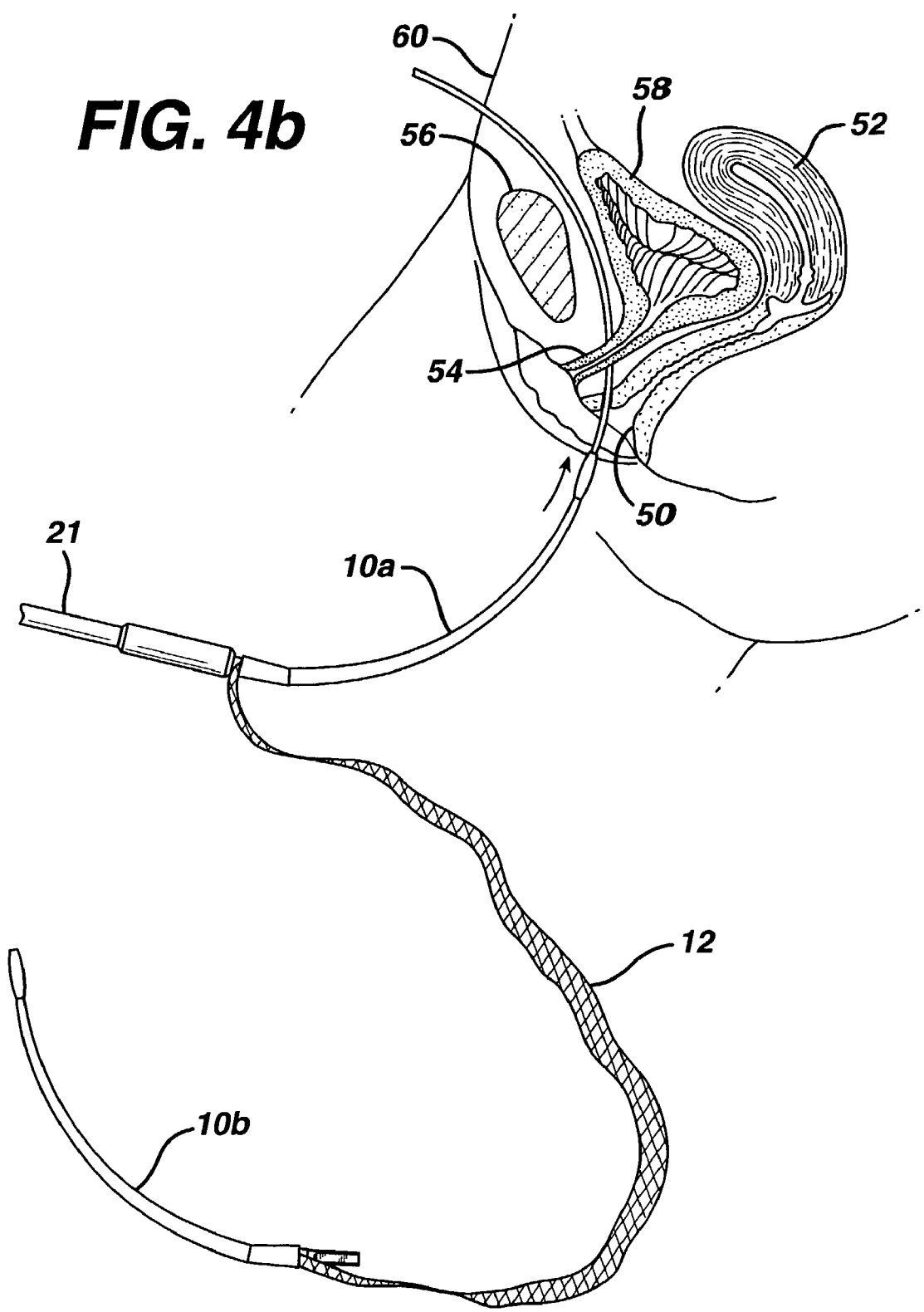

US 7,226,407 B2

SURGICAL INSTRUMENT AND METHOD FOR TREATING FEMALE URINARY INCONTINENCE

CROSS REFERENCE TO RELATED APPLICATION

The present invention is a continuation of U.S. patent application Ser. No. 09/873,571 filed on Jun. 4, 2001, now U.S. Pat. No. 7,121,997, which is a continuation-in-part of U.S. patent application Ser. 09/521,801 filed Mar. 9, 2000, now U.S. Pat. No. 6,273,852, and which claims benefit of earlier-filed U. S. provisional patent application, Ser. No. 60/138,231, filed on Jun. 9, 1999, which are incorporated by reference in their entirety herein.

BACKGROUND OF THE INVENTION

1. Field of the Invention

The present invention relates generally to a surgical instrument and a method for treating female urinary incontinence and in particular to a needle and mesh configuration for creating a sling beneath the urethra.

2. Background Discussion

Women account for more than 11 million of incontinence cases. Moreover, a majority of women with incontinence suffer from stress urinary incontinence (SUI). Women with SUI involuntarily lose urine during normal daily activities and movements, such as laughing, coughing, sneezing and regular exercise.

SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle, shying away from social situations.

U.S. Pat. No. 5,112,344 describes a method and apparatus for treating female incontinence. The surgical instrument for the application of a filamentary element into the body comprises a tubular shaft having a handle at one end and a flexible needle slidably receivable in the shaft and adapted at one end to receive a filamentary element. The method of treating female incontinence comprises looping a filamentary element between the wall of the vagina and the rectus abdominis sheath in the anterior wall of the abdomen whereby it passes to each side of the urethra, tightening the loop to bring the vaginal wall and the urethra into the correct spatial relationship to the pubis allowing the development of scar tissue between the vaginal wall and the anterior wall of the abdomen pubic symphysis and removing the filamentary element.

U.S. Pat. No. 5,899,909 discloses a surgical instrument comprising a shank having a handle at one end and connecting means at the other end to receive, one at a time, two curved needle-like elements which are connected at one end to one end of a mesh intended to be implanted into the body. In practice, the mesh is passed into the body via the vagina first at one end and then at the other end at one side and the other, respectively, of the urethra to form a loop around the urethra, located between the urethra and vaginal wall. The mesh is extended over the pubis and through the abdominal wall and is tightened. The mesh ends are cut at the abdominal wall, and the mesh is left implanted in the body. This trans-vaginal procedure is exemplified by the TVT product sold by the Gynecare franchise of Ethicon Inc., a Johnson & Johnson Company, of Somerville, N.J., USA. In this procedure two 5 mm needles pass a PROLENE mesh trans-vaginally and through the abdomen to create a tension-free support around the mid urethra. U.S. Pat. No. 5,899,909 is incorporated herein by reference in its entirety.

An alternate method to treat SUI is the sling procedure. In this procedure a needle or other suture-retrieving device is first inserted through the abdomen, above the pubic bone. The needle is guided behind the pubic bone, through the subrapubic fascia around the urethra, and out of the body through an incision in the anterior vaginal wall. At this point sutures are attached to the needle(s) and pulled up back through the abdominal cavity, where the sutures are fastened to the rectus muscle.

Techniques for protecting against the puncture of the internal structures during this type of procedure have included laparoscopic procedures. This involves making an incision in the abdomen and inserting a video scope to watch the progress of the needles as they pass through the abdominal cavity. These additional incisions are not optimal for the patient. Also, the needles which pass through the abdomen are not designed to capture a mesh but rather a suture which has been previously attached to the mesh or harvested fascia. These needles are generally in the diameter range of about 0.090 ins. to about 0.120 inches. Therefore, the needles do not create a large channel through the fascia. The channel is only wide enough to pass the suture. Accordingly, the sutures do not possess the elongation properties of the PROLENE mesh and therefore can not provide the tension-free support of the TVT. Also attaching a mesh directly to these needles is not optimal because it is very difficult, if at all possible, to pull the mesh through the narrow channel created by the needle.

It would be beneficial to provide a surgical system for use in implanting a mesh within a female body to prevent incontinence that can be implanted either through a trans-vaginal approach or a trans-abdominal approach.

This invention addresses that need and overcomes the deficiencies of the prior art.

SUMMARY OF THE INVENTION

The invention overcomes the deficiencies of the prior art and provides for a surgical apparatus and a method for the treatment of female stress urinary incontinence. The invention provides a surgical instrument comprising a handle at one end and connecting means at the other end to receive, one at a time, two curved needle-like elements, each of which have a blunt tip and a constant or varying diameter. The distal end of the needle comprises an interlocking coupling means for accepting a guide needle or, alternatively, a mesh.

In one embodiment each curved needle connects at its proximal end to separate ends of a mesh to be implanted within the body. A guide needle, similar in structure to a Stamey needle, is passed through the abdomen and behind the pubic bone, passes along one side of the urethra and to an incision site at the anterior vaginal wall. After the guide needle exits the body through the vagina, the guide needle couples to the distal end of the curved needle. The curved needle is then pushed back through the vagina and through the fascia, following the path of the guide needle. The curved needle and first end of the mesh pass over the pubis and through the abdominal wall. The guide needle is again passed behind the pubic bone from the abdomen, passes along the other side of the urethra to the incision site in the vaginal wall. The guide needle again couples to the distal end of the second curved needle, which then passes through the vagina and fascia, following the second path created by the guide needle. The second end of the mesh is extended over the pubis and through the abdominal wall. The mesh ends are cut at the abdominal wall, and the mesh is left in the body, creating a tension-free support between the vaginal wall and the mid urethra.

In an alternate embodiment a curved needle is passed through the abdomen and behind the pubic bone, passes along one side of the urethra and to an incision site in the anterior vaginal wall. After the curved needle exits the body through the vagina, the distal end of the curved needle couples to one end of the mesh to be implanted within the body. The curved needle is then pulled back through the vagina and through the fascia, following the path it originally created. The curved needle and first end of the mesh pass over the pubis and out through the abdominal wall. The first end of the mesh de-couples from the curved needle and the needle is again passed behind the pubic bone from the abdomen, passes along the other side of the urethra to the incision site in the vaginal wall. The needle couples to second end of the mesh and is then pulled back through the vagina and fascia, following the second path created by the needle. The second end of the mesh is extended over the pubis and through the abdominal wall. The mesh ends are cut at the abdominal wall, and the mesh is left in the body, creating a tension-free support between the vaginal wall and the mid urethra.

The invention is also compatible for use in a trans-vaginal approach as described in U.S. Pat. No. 5,899,909.

The object of the invention is to provide a surgical instrument that implants a mesh for treatment of SUI and is capable for using in a trans-vaginal or a trans-abdominal procedure.

An advantage of the invention is that it is useful across different medical specialties depending on preferred surgical approaches.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIGS. 3b–d bare alternate embodiments of a connector for use in FIG. 3a;

FIGS. 4a–j diagrammatically illustrate several surgical steps of a trans-abdominal method utilizing two needles and guide needle according to the invention to treat SUI;

DETAILED DESCRIPTION OF THE INVENTION

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways.

The invention discloses an apparatus and method for treating SUI. A mesh or tape is passed through pelvic tissue and positioned between the urethra and vaginal wall, creating a supportive sling. The mesh provides a structure means for tissue ingrowth and thereby provides a newly created body tissue supporting means for the urethra. When pressure is exerted upon the lower abdomen, such as during a cough or sneeze, the mesh provides support to the urethra, allowing it to keep its seal and prevent the unwanted discharge of urine.

Figure 1:
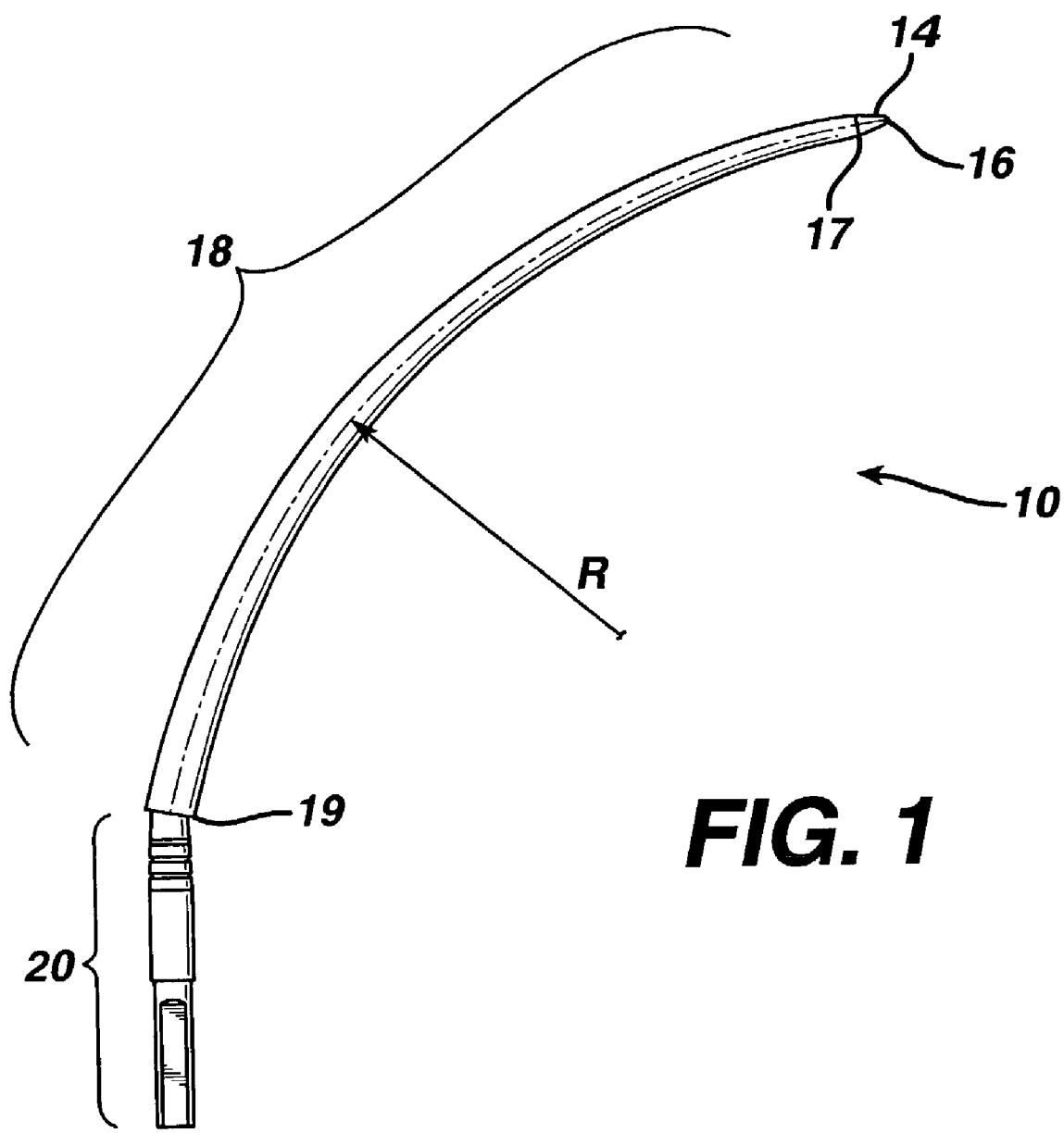
FIG. 1 is a side view of the needle in one embodiment thereof.
Figure 2A:
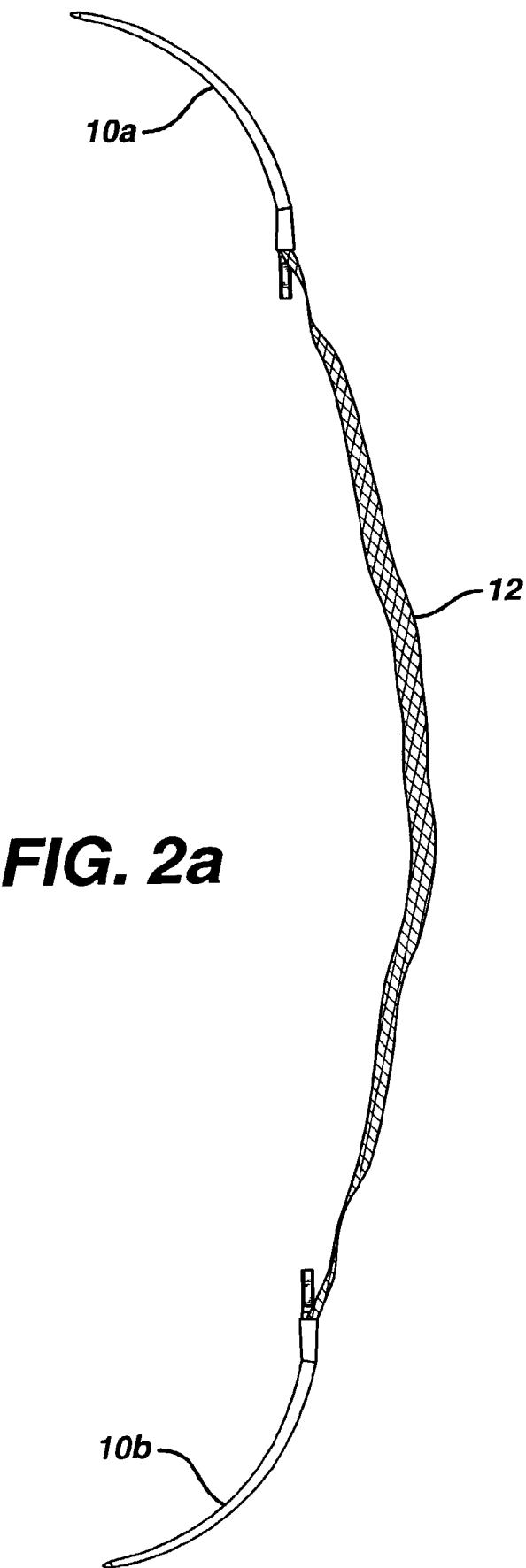
FIG. 2a is a side view of two needles and a mesh interconnecting the needles.

Referring to FIGS. 1 and 2a, in one embodiment the surgical instrument comprises a needle-like element 10 that attaches to a mesh 12. Needle element 10 defines a certain radius R to perform the surgical procedure discussed herein. The distal end of needle element 10 terminates at a conical section 14 having a tip 16. Alternate configurations, such as a blade-like, arrow or burr tips are also possible. Preferably, tip 16 is blunt, wherein the tip 16 has a radius of about 0.6 millimeters. A blunt tip is preferred since it is less likely to stick in bone or penetrate bladder wall tissue or blood vessel wall tissue as will be appreciated from the method of implanting the mesh as described below.

The proximal end of needle 10 terminates in an attachment segment 20 that is adapted to mate and lock into a handle 21 as disclosed in U.S. Pat. No. 5,899,909.

Disposed between tip 14 and segment 20 is a curved shaft segment 18 having a distal end 17 and a proximal end 19. The shape of shaft 18 extends substantially a quarter of a circle in order to follow substantially the profile of the pubis between the vagina and the abdominal wall. For the purposes of the method as will be discussed in more detail below, shaft 18 has a preferred radius R of about 106 millimeters. The diameter of shaft 18 may be constant, for example, about 5 mm. Alternatively, the diameter of segment 18 may transition from a smaller diameter at distal end 17 to a larger diameter at proximal end 19. The minimum diameter of distal end 17 may be as small as 0.5 mm due to the minimal stresses at this point. The minimal diameter of proximal end 19 is about 4 mm.

Needle 10 is preferably tubular with a circular cross section and is made from a material that is compatible with the human body. Preferably, needle 10 is made from AISI 303 stainless steel. The surface of shaft 18 may be smooth, preferably polished, to facilitate penetration of the soft tissue. Alternatively, the surface of needle 10 may have a somewhat rougher surface. A rougher surface would result in slightly additional tissue trauma, which in turn stimulates fibroblast activity around the mesh 12. The surface of needle 10 may also be darkened in shade or color to provide higher visibility while in place in the body during a cystoscopy.

Needle 10 may be manufactured as a single, continuous unit, or alternatively, curved portion 18 may be manufactured separately from linear portion 20. In this manner the two pieces would attach using any conventional attaching means, such as, screwing, or other conventional means as is known to those skilled in the art.

Figure 2B:
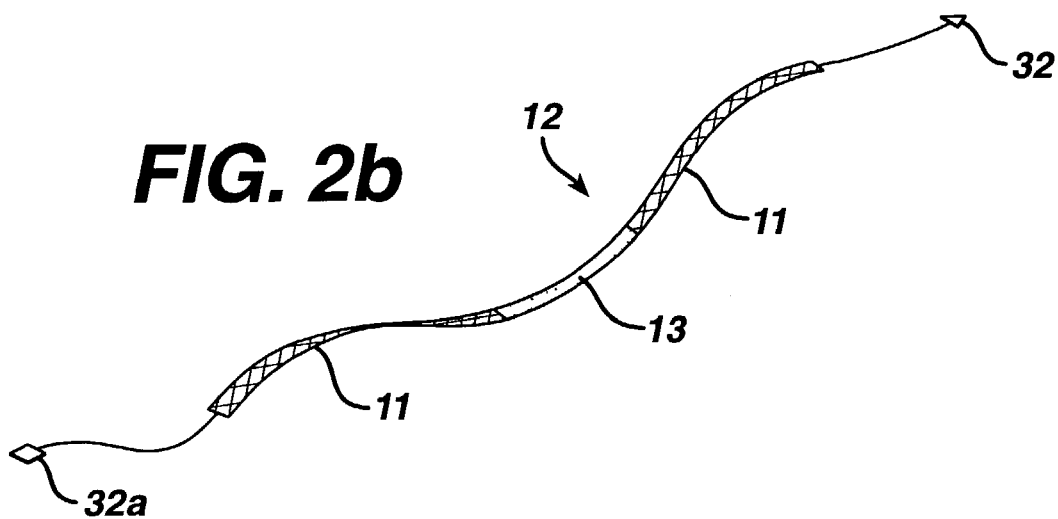
FIGS. 2b–d are alternate embodiments of the mesh and connecting means between the mesh and needle.
Figure 2C:
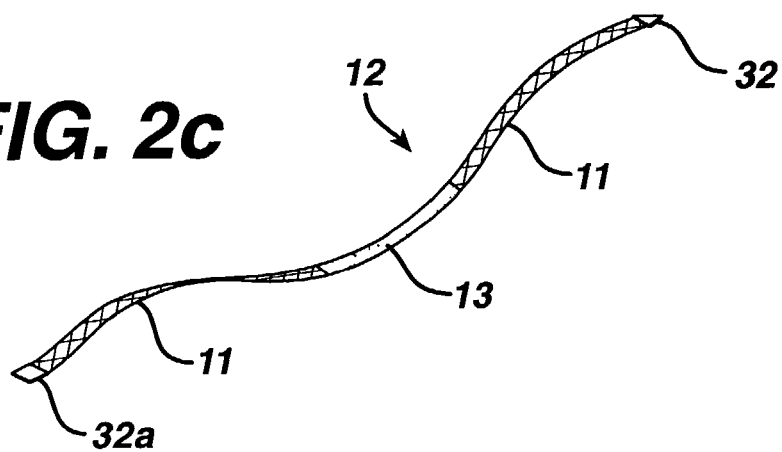
Figure 2D:
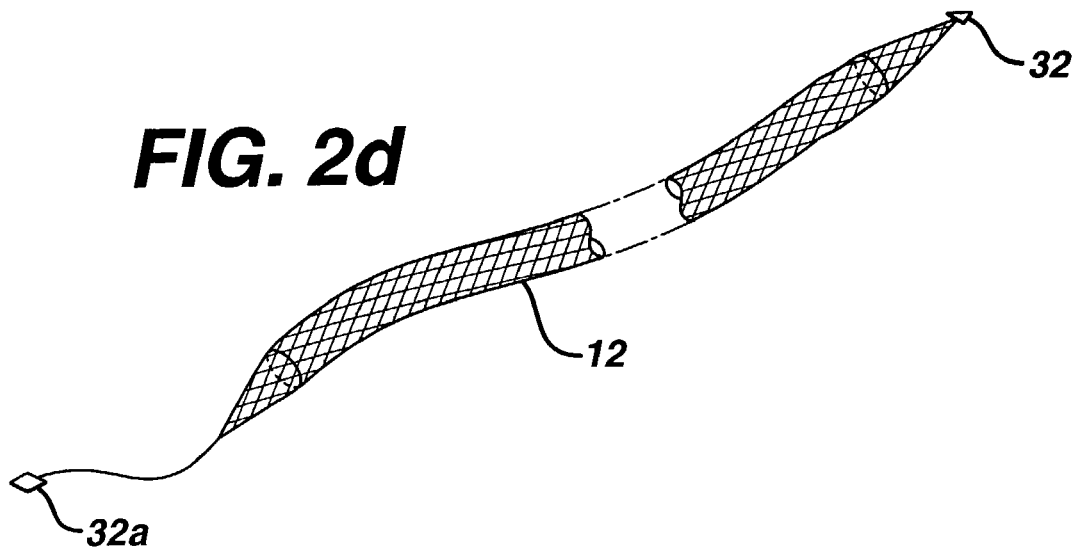

Referring to FIGS. 2a–d, mesh 12 comprises any tissue-compatible synthetic material, or any natural material, including, but not limited to, autologous, allograft, xenograft, a tissue engineered matrix, or a combination thereof. An exemplary synthetic material is PROLENE® polypropylene mesh, a mesh having a thickness of 0.7 mm and openings of about 1 mm manufactured by Ethicon, Inc., Somerville, N.J., U.S.A. This material is approved by the U.S. Food and Drug Administration for implantation into the human body. A still further embodiment of the mesh 12 is a combination of a synthetic material 11 and a natural material 13 centered between the synthetic material 11 as shown in FIGS. 2b–c. A still further embodiment of the mesh 12 includes a combination of synthetic material 11 and natural material 13, whereby the natural material is placed over or incorporated within a generally central portion of the synthetic material 11. One advantage of the mesh configurations is that natural material 13 is along the center region of mesh 12 so that after installation of mesh 12, natural material 13 is positioned below the urethra and eliminates possible erosion issues at the interface of the urethra and mesh. Natural material 13 may be connected to the synthetic material 11 by means of sewing, a bio-compatible glue, cell culturing techniques or other known means.

Mesh 12 may be of any convenient shape that suits the intended purpose of the invention. An exemplary width is about 1 cm and the length would be dependent upon the size of the female undergoing the procedure. Mesh 12 may be single or double ply, generally planar in structure, or tubular (FIG. 2d) to provide additional supporting strength and more surface area on which tissue fibers may attach.

Moreover, mesh 12 may consist of different types of material, such as a bioabsorbable and non-bioabsorbable material. Mesh 12 may also be coated with an antimicrobial additive to prevent or minimize infection and a lubricous coating, for example, a bioabsorbable hydrogel, to facilitate the mesh passing through the tissue as discussed below. Preferably, mesh 12 is covered by a removal plastic sheath as disclosed in U.S. Pat. No. 5,899,909. The mesh may also be made radio-opaque and/or of a contrasting color to the body tissue to allow for future diagnostic visualization.

In one embodiment mesh 12 may be attached to needle segment 20 by means of tying, gluing or other suitable attaching means. Preferably, a bio-compatible heat shrink tube fixes mesh 12 onto needle portion 20, FIG. 2a.

Figure 3A:
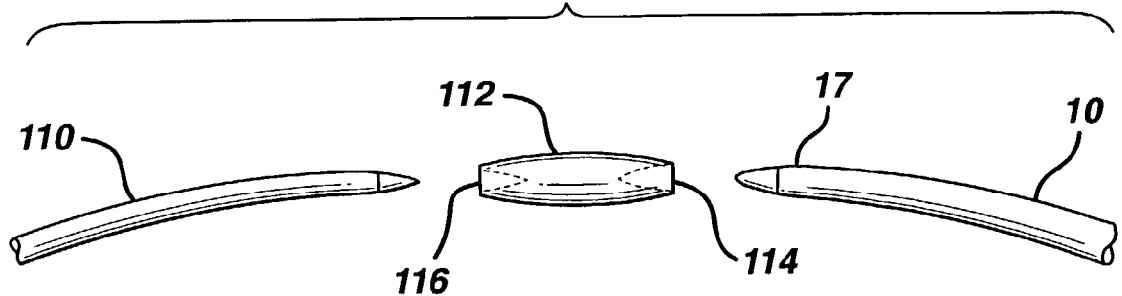
FIG. 3a is an assembly diagram for two needles and a connector.

FIG. 3a illustrates a needle 10 for use in conjunction with a guide needle 110 and coupler 112. Guide needle 110 may be configured to have a similar radius R as needle 10. Preferably, guide needle 110 has a smaller diameter, about 2 mm. It is possible, however, for guide needle 110 to have the same diameter as needle 10. A coupler 112 acts as an interfacing element useful to couple guide needle 110 to needle 10. Coupler 112 is substantially elliptical-shaped having a first bore opening 114 for accepting distal end 17 and a second bore opening 116 for accepting the distal end of guide needle 110. Preferably, openings 116 and 114 are configured to allow for a press fit connection with needles 110 and 10, respectively. Alternatively, openings 114 and 116 may comprise a bio-compatible glue or high-friction material to facilitate a strong connection between the needles 10/110 and coupler 112. Coupler 10 may be made from any bio-compatible metal, such as stainless steel or polyurethane, silicone, rubber or other similar compound.

Figure 3B:
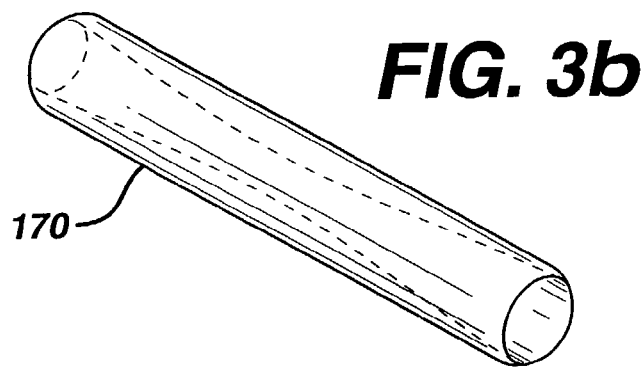
Figure 3C:
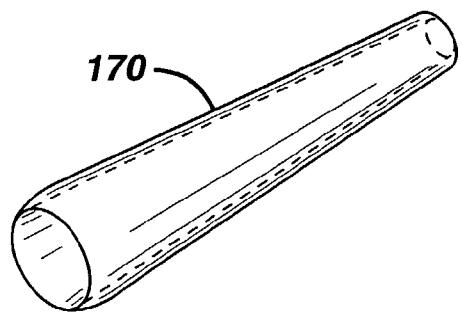
Figure 3D:
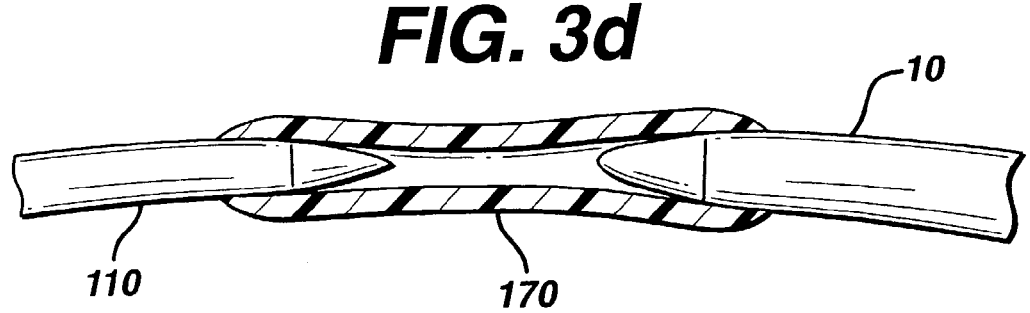
Figure 4A:
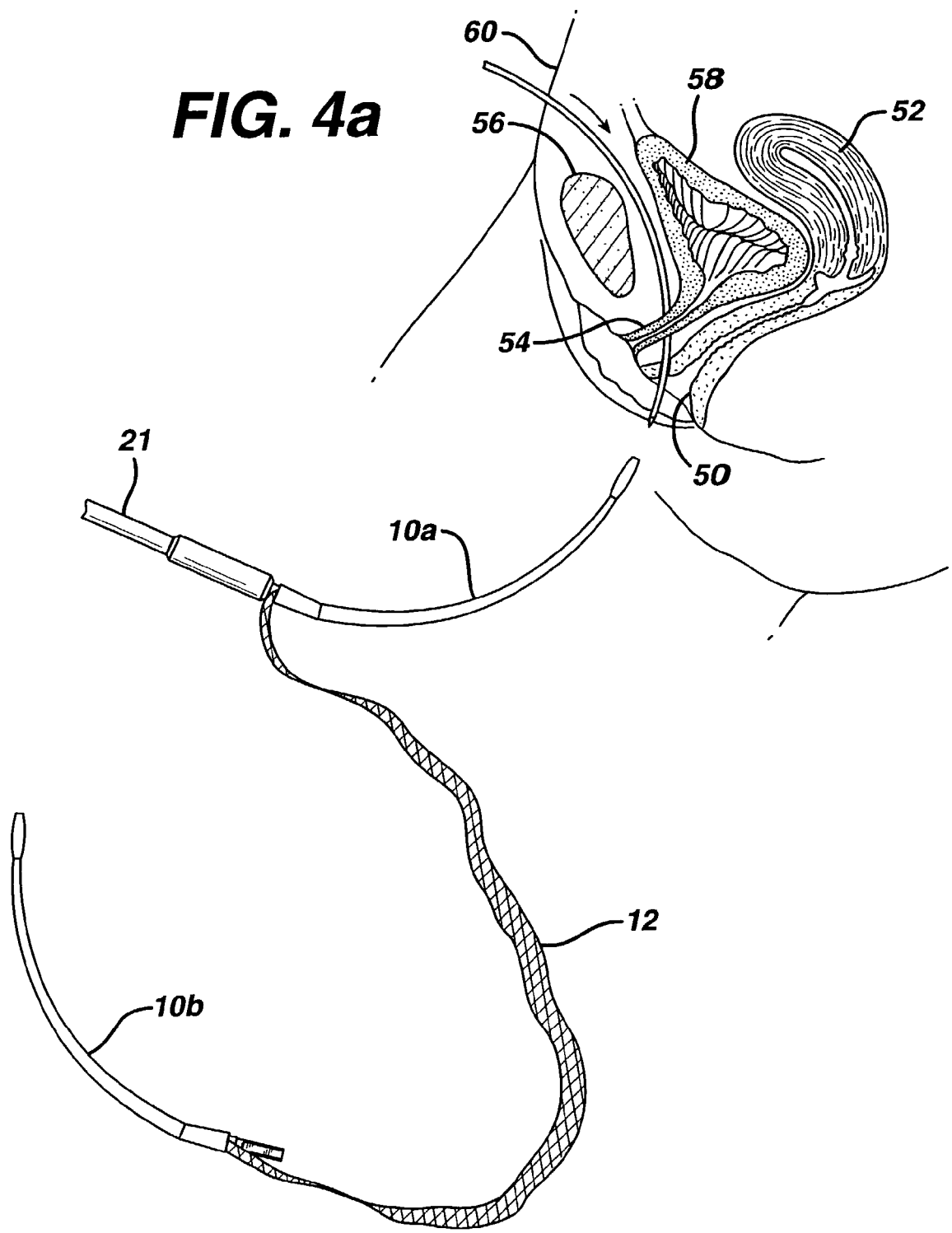
Figure 4C:
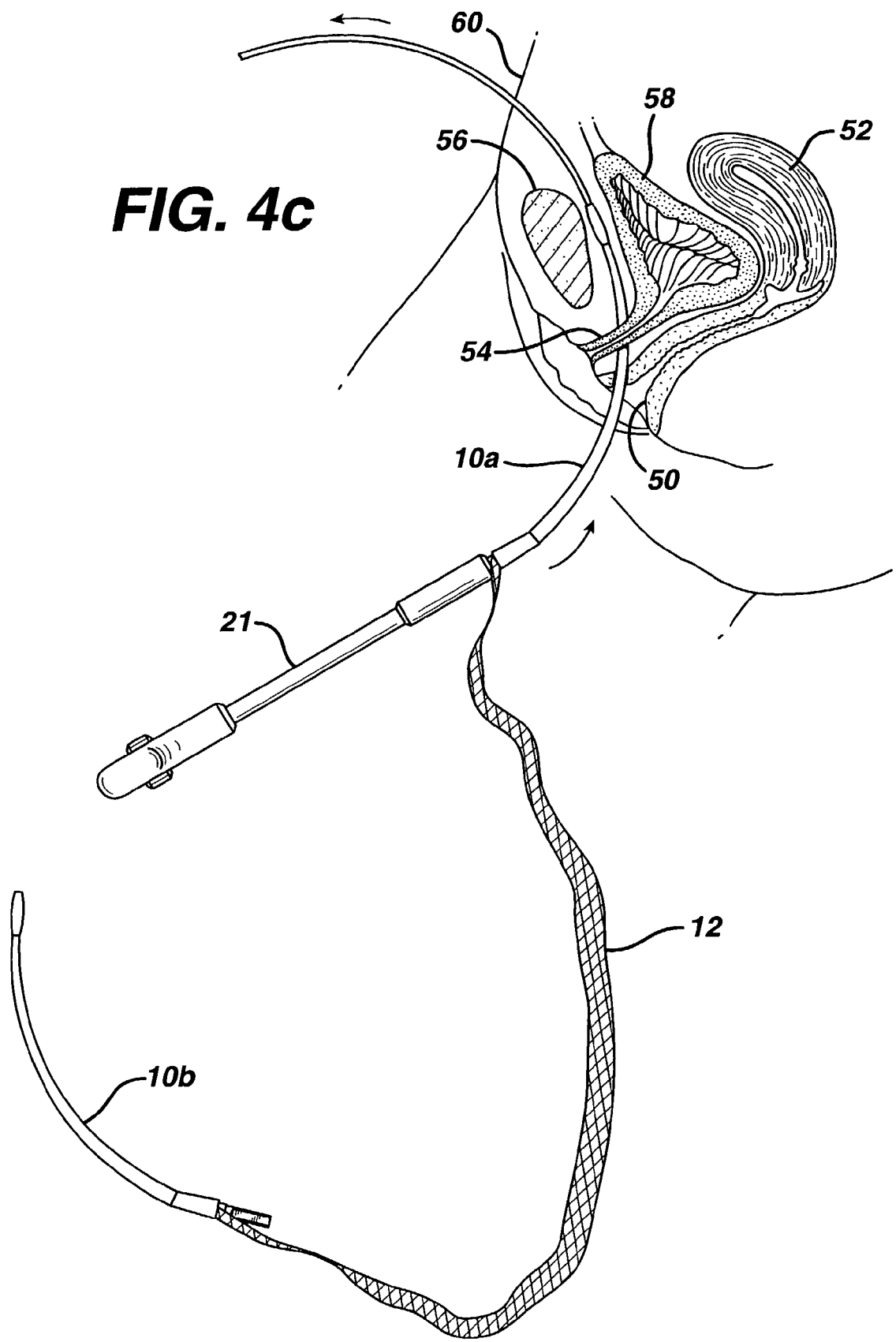
Figure 4D:
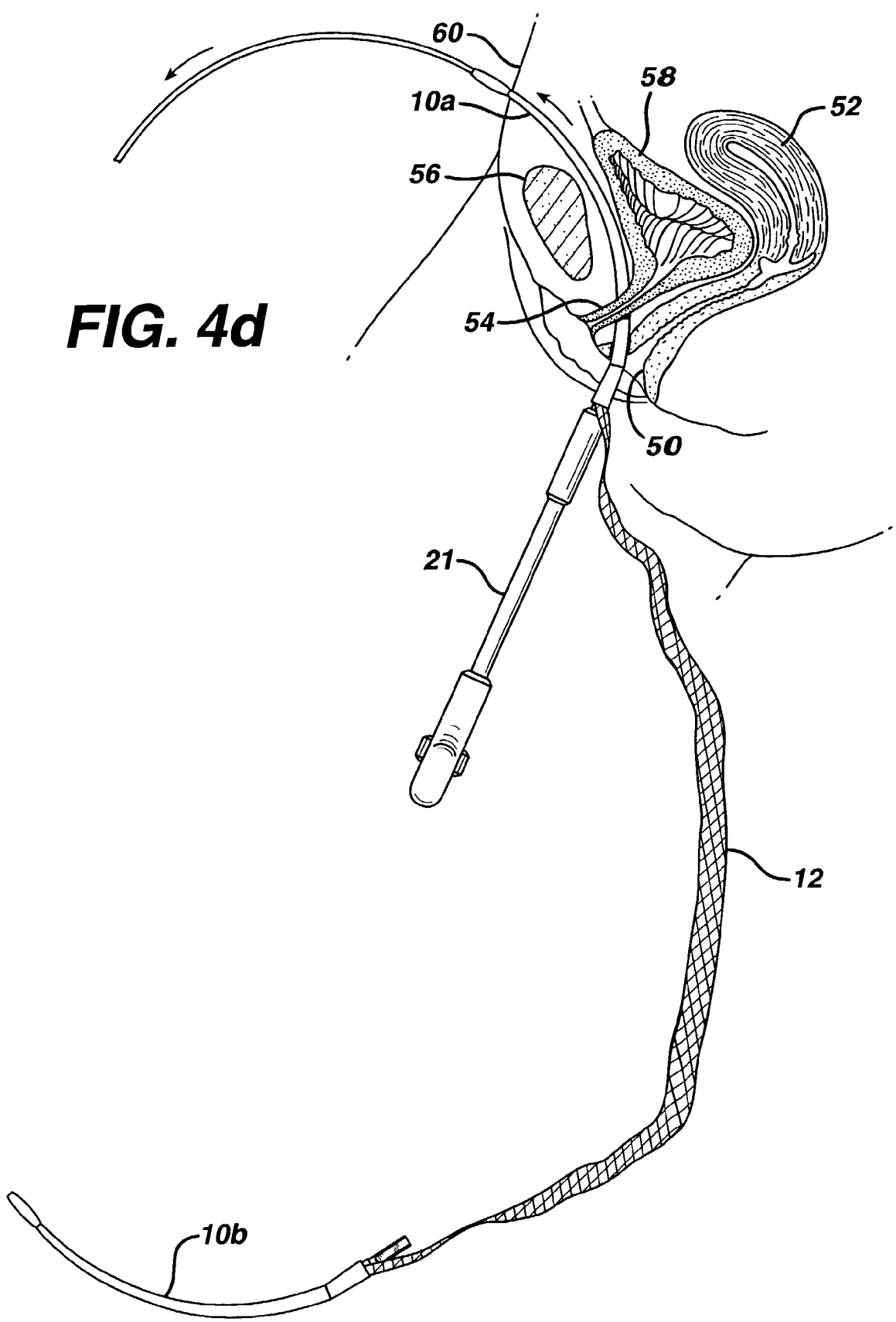
Figure 4E:
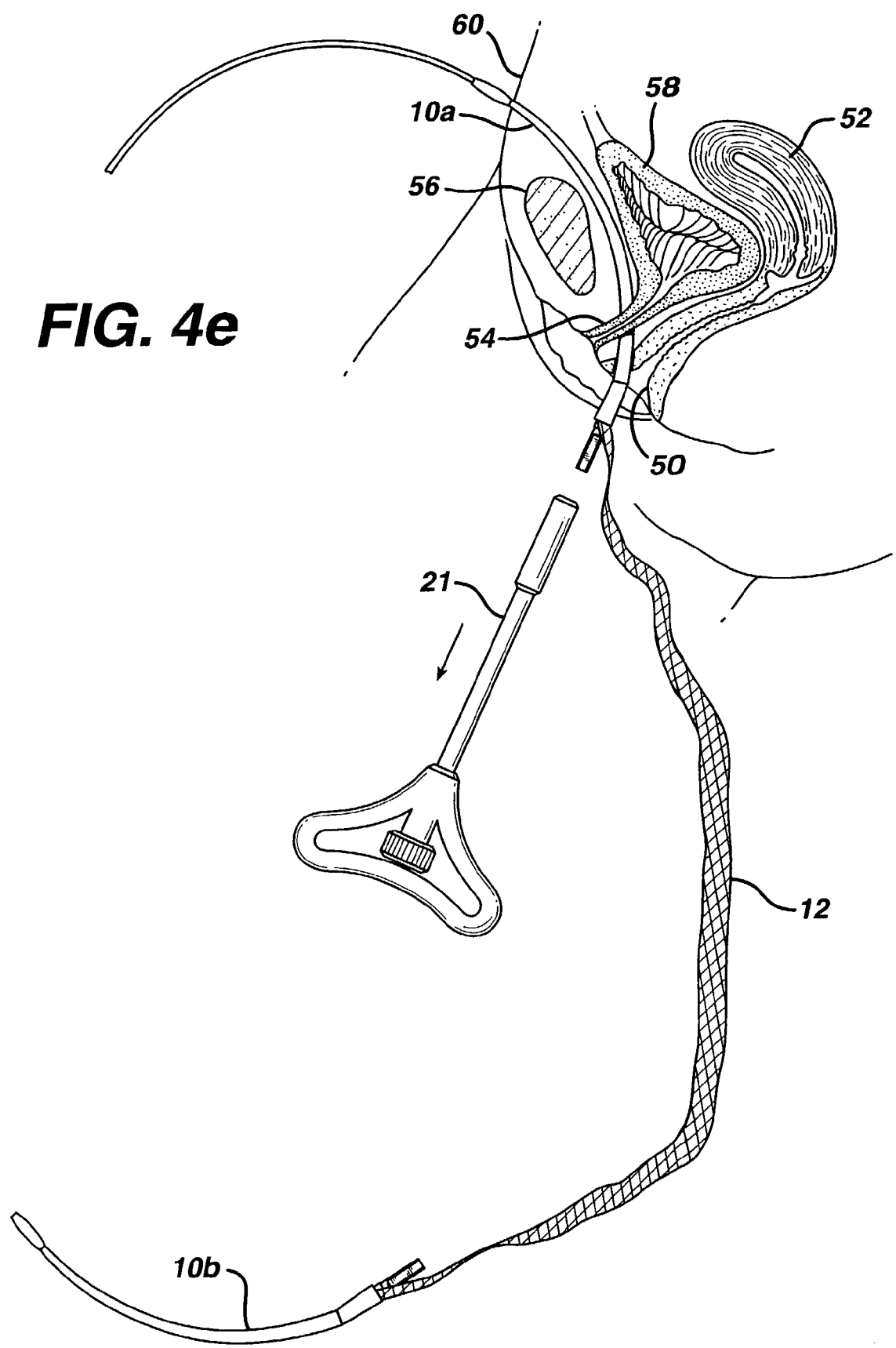
Figure 4F:
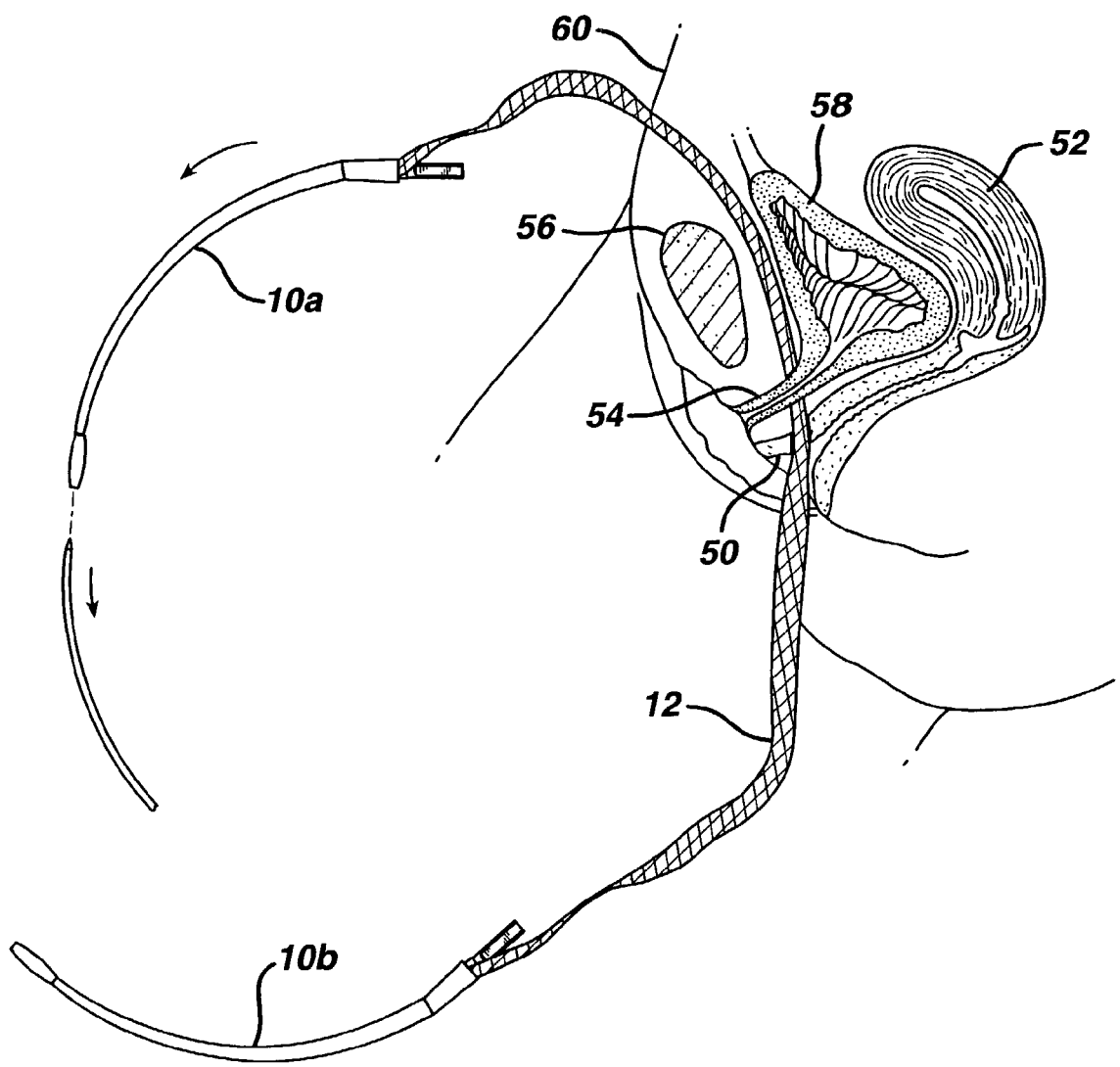
Figure 4G:
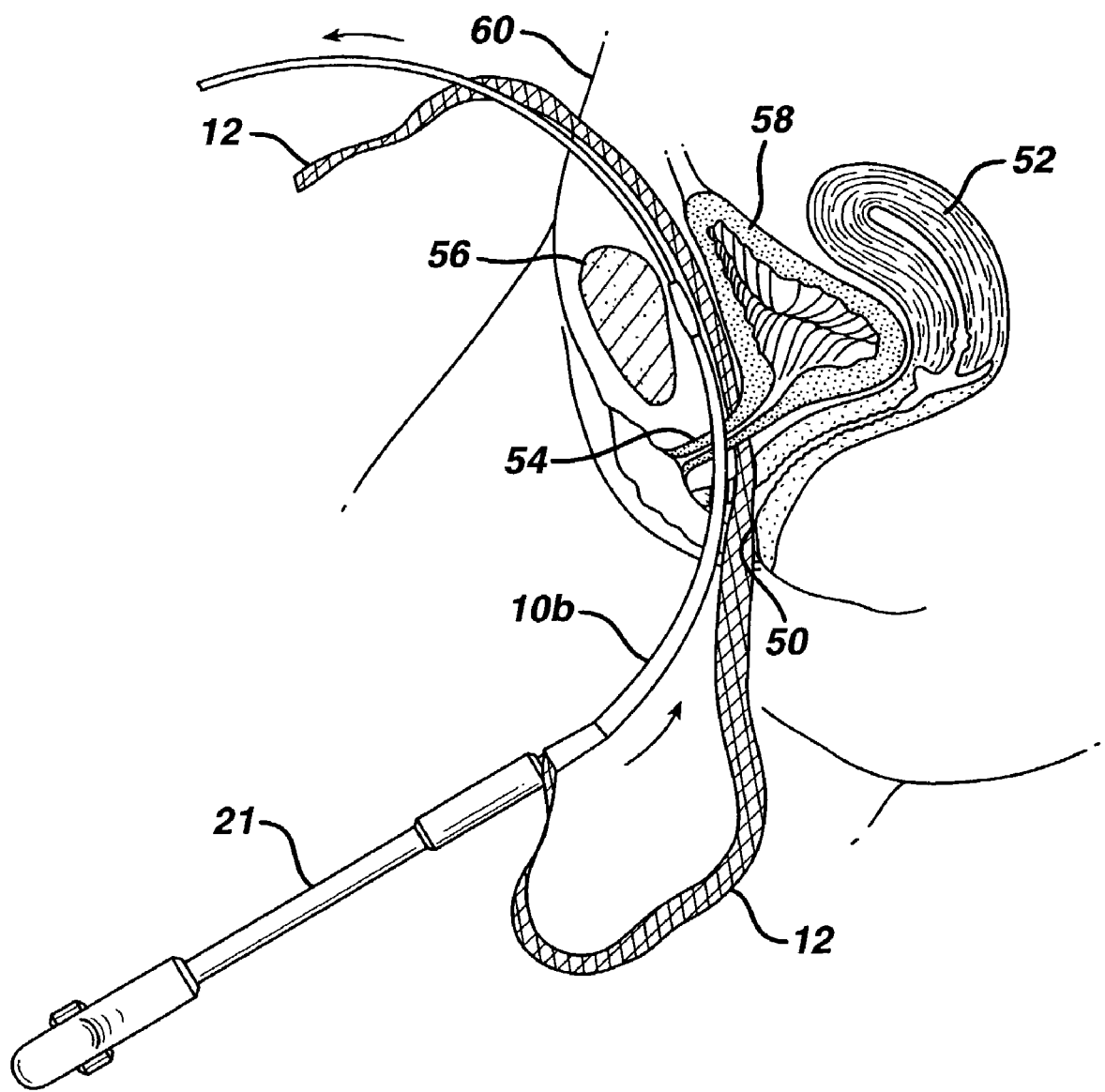
Figure 4H:
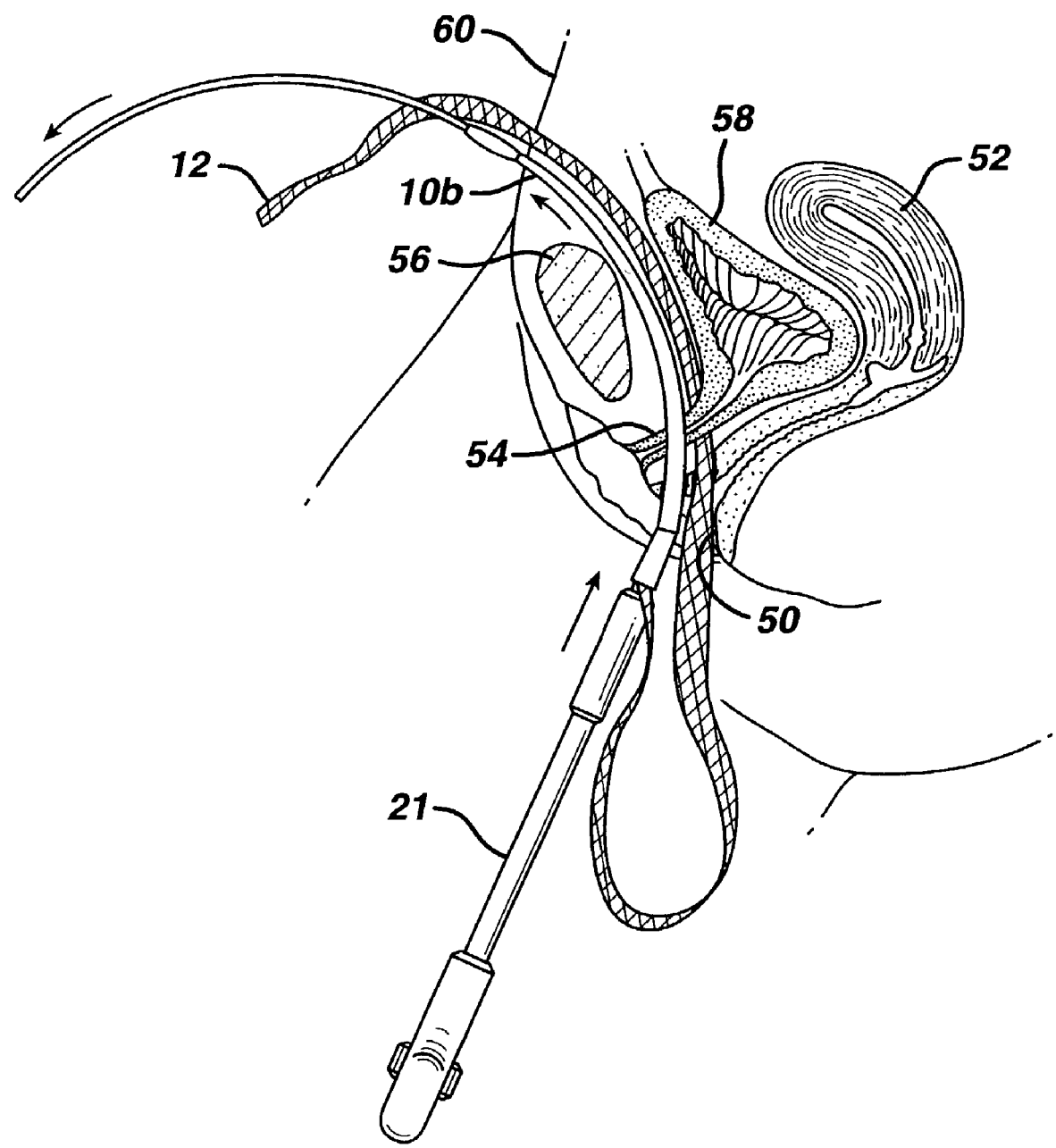
Figure 4I:
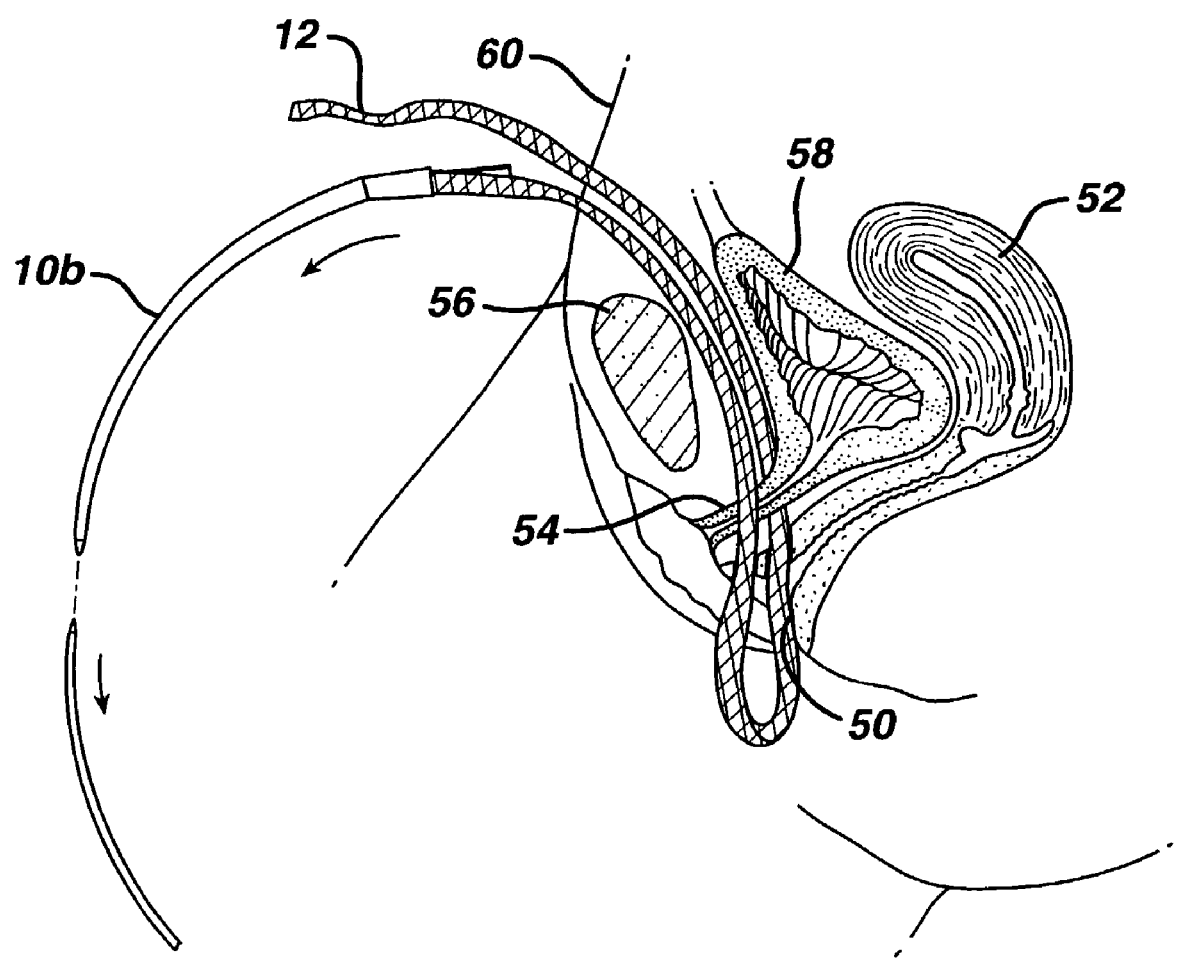
Figure 4J:
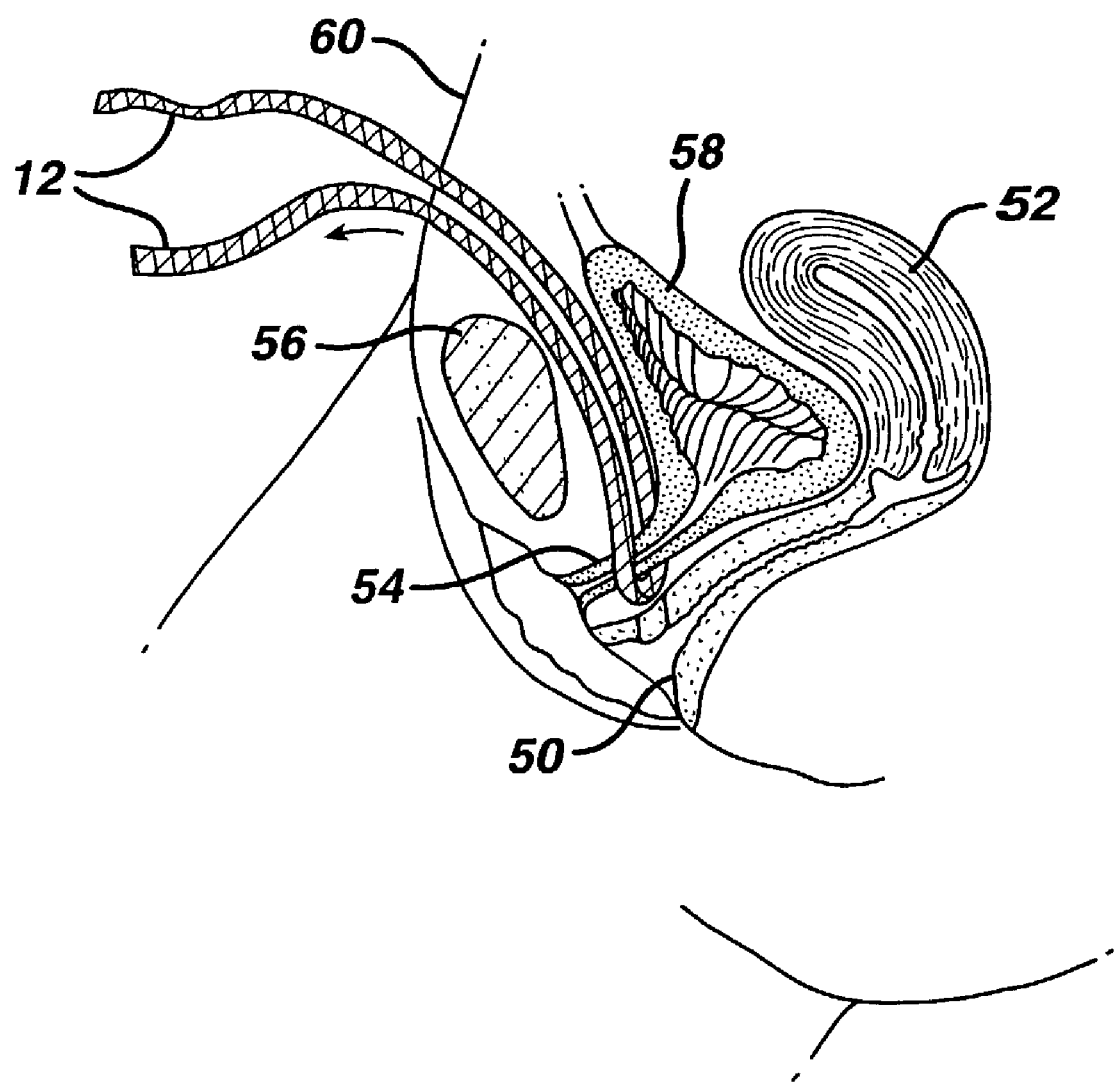

FIGS. 3b–d illustrate alternate connector means utilizing a high friction tube 170, such as Tygon. FIG. 3b discloses a tube having a constant O.D., but a varying I.D. The larger I.D. would accept needle 10 and the smaller I.D. accepts the guide needle 110. FIG. 3c illustrates a tube 172 having both a varying O.D. and I.D. As the needles are placed within the tube the decreasing I.D. compresses around the distal ends of the respective needles and the high coefficient of friction securely anchors the needles. FIG. 3d illustrates the needles within the tube 172. Preferably, the ends of tube 170 and 172 are tapered to eliminate any abrupt surface that adds additional drag to the needles as they are pulled through the abdominal cavity.

The surgical procedure for trans-abdominally implanting mesh 12 using two needles is shown in FIGS. 4a–j. In the figures the relevant parts of the female lower abdomen are disclosed, the vagina being 50, the uterus 52, the urethra 54, the pubic bone 56, the urinary bladder 58 and the abdominal wall 60. A guide needle 110 penetrates the abdominal wall 60, anterior to the pubic bone 56, FIG. 4a and follows the contour of the pubic bone 56 to one side of the urethra 54 and exits the body through an incision having been made in the anterior wall of the vagina 50. Coupler 112 attaches to the distal end of guide needle 110, extending out from the body, and needle 10a, FIG. 4b. One end of mesh 12 is attached to the proximal end of needle 10a. The surgeon then retracts guide needle 110 back through the abdomen and advances needle 10a through the vaginal incision following the same path guide needle 110 created, FIG. 4c. The needles pass through the vaginal wall and through the soft tissue on one side of the urethra 54, the needles then according to FIG. 4d being passed close to the back of the pubic bone 56, through additional layers of fat, muscle and fascia, and then out the abdominal wall 60 above the pubic bone 56. The surgeon uncouples handle 21 from the needle 10a and pulls needle 10a out of the body through the abdominal wall 60, FIG. 4e.

Guide needle 110 is disconnected from needle 10a, and the surgeon repeats the same procedure, but passing the guide needle 110 on the opposite side of the urethra 54, FIGS. 4f–j, to complete the implantation of the mesh between the mid-urethra and vaginal wall using needle 10b.

FIGS. 8a–i illustrate an alternate preferred embodiment. A first guide needle 110a penetrates the abdominal wall 60, anterior to the pubic bone 56 and follows the contour of the pubic bone 56 to one side of the urethra 54 and exits the body through an incision having been made in the anterior wall of the vagina 50. A second guide needle 110b penetrates the abdominal wall 60, anterior to the pubic bone 56 and follows the contour of the pubic bone 56 to the opposite side of the urethra 54 as guide needle 110a and exits the body through an incision having been made in the anterior wall of the vagina 50, FIG. 8a. At this point, the surgeon may perform a single cystoscopy to confirm the integrity of the bladder 58. Couplers 112a,b attach to the distal ends of needles 10a,b. Needle 10a, having one end of mesh 12 attached to the proximal end of needle 10a attaches to guide needle 110a via coupler 112a, FIG. 8b. The surgeon then retracts guide needle 10a back through the abdomen and advances needle 10a through the vaginal incision following the same path guide needle 110a created. The needles pass through the vaginal wall and through the soft tissue on one side of the urethra 54, the needles being passed close to the back of the pubic bone 56, through additional layers of fat, muscle and fascia, and then out the abdominal wall 60 above the pubic bone 56, FIGS. 8c–d. The surgeon uncouples handle 21 from the needle 10a and pulls needle 10a out of the body through the abdominal wall 60, FIG. 8e.

The surgeon repeats the same procedure, but removing guide needle 110b and advancing needle 10b on the opposite side of the urethra 54, to complete the implantation of the mesh between the mid-urethra and vaginal wall using needle 10b, FIGS. 8f–i.

Figure 5A:
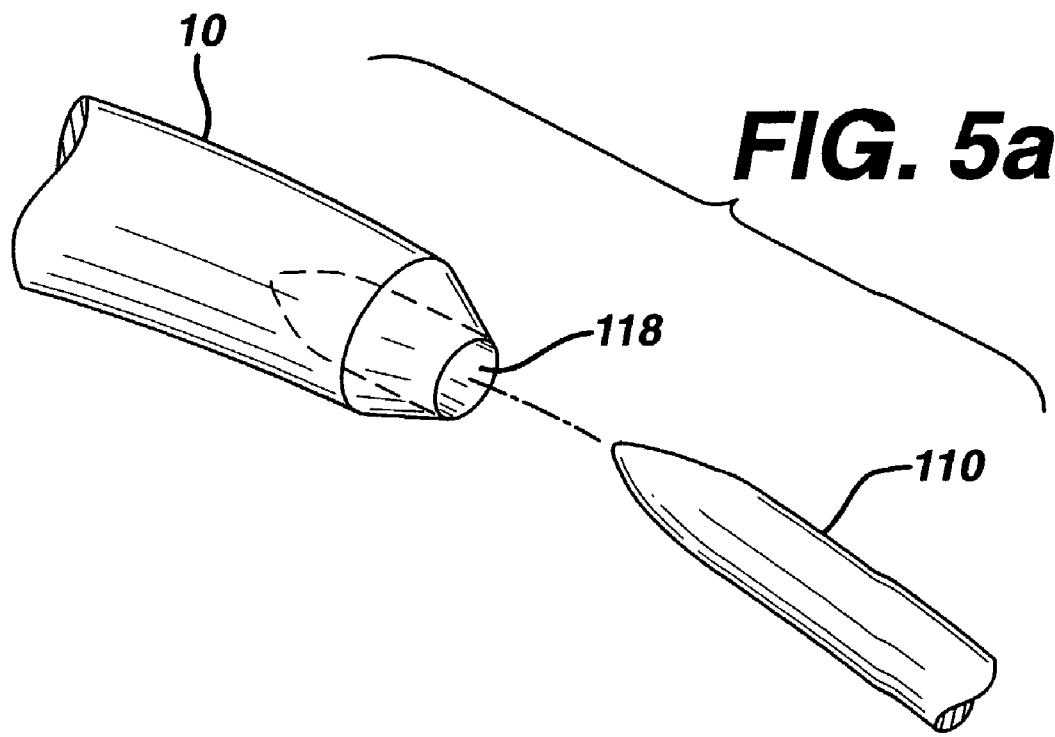
FIGS. 5a–d illustrate alternate embodiments of coupling the guide needle to the needle.
Figure 5B:
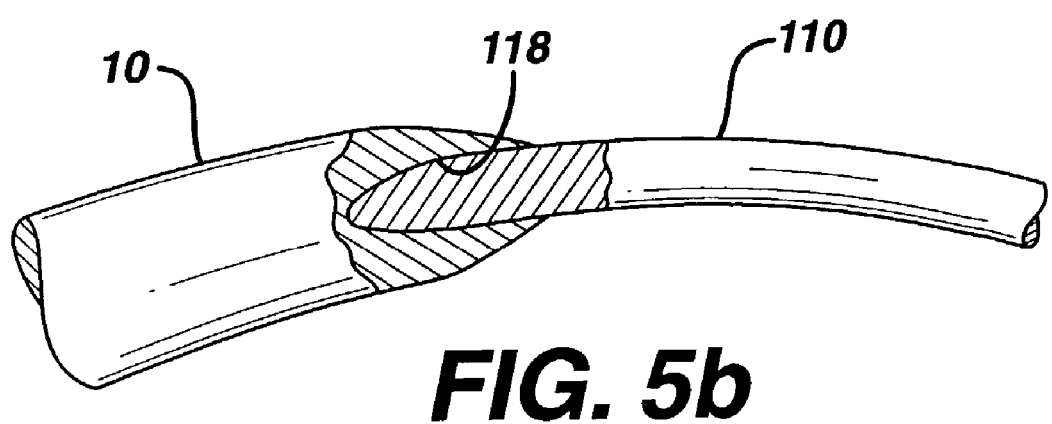

FIGS. 5a–d illustrate alternate embodiments for coupling needle 10 to guide needle 110 to implant a mesh 12 trans-abdominally as indicated above. In FIGS. 5a–b, the distal end of needle 10 is modified to include a bore opening 118 to allow for a press fit connection with the distal end of guide needle 110. Alternatively, bore-opening 118 may comprise other connection means, such as glue or a high-friction material.

Figure 5C:
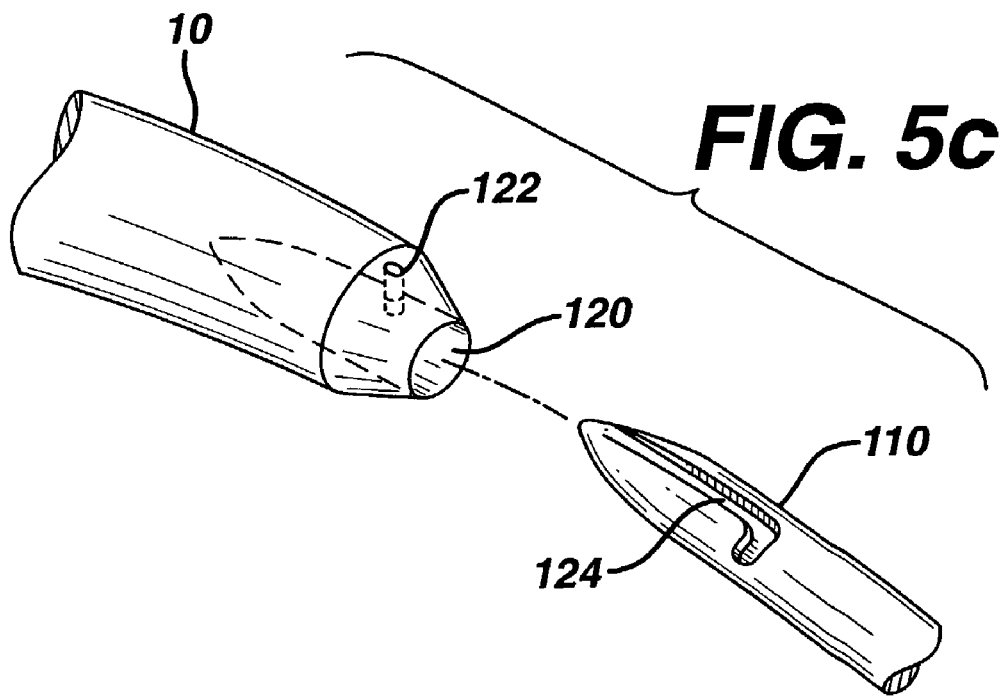
Figure 5D:
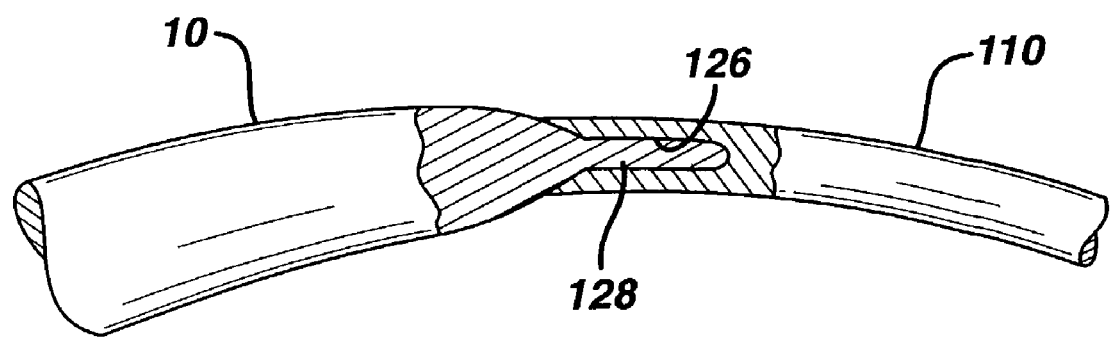

In FIG. 5c, the distal end of needle 10 is modified to include a bore opening 120 and a locking pin 122. Guide needle 110 is modified to include an L-shaped groove 124. The distal end of guide needle 110 inserts into opening 120 and groove 124 engages locking pin 122 and locks thereto with a quarter-turn twist. FIG. 5d illustrates a bore opening 126 in guide needle 110 to accept a protruding element 128 at the distal end end needle 10. Protruding element 128 press fits into bore opening 126.

One advantage of the embodiment shown in FIG. 3 is that the needle 10 can be used for either a trans-abdominal approach or a trans-vaginal approach. In this approach, a kit comprising two needles 10, attached to a mesh 12, at least one coupler and at least one guide needle may be distributed for use by multiple surgeon specialists. For example, a gynecologist may prefer the trans-vaginal approach and will simply discard the connector and guide needle from the kit. On the other hand, a urologist may prefer the trans-abdominal approach and utilize the connector(s) and guide needle(s).

Referring now to FIGS. 6a–h, an alternate embodiment of the invention utilizes the needle 10 to penetrate the abdominal wall 60 and couple to the mesh 12. In this embodiment, the mesh 12 is modified to create a connection means for connecting to the distal end of the needle 10. The connection means is preferably detachable so that when the mesh is pulled out of the abdominal wall, the mesh may be detached from the needle and the needle reused to retrieve the other end of the mesh. This embodiment allows for the use of a single needle for the procedure. This embodiment also allows for the use of a mesh constructed, at least in part, of natural materials, which are otherwise not suitable in the pre-affixed embodiment due to the inability of the natural material to survive extended periods in inventory.

Figure 6A:
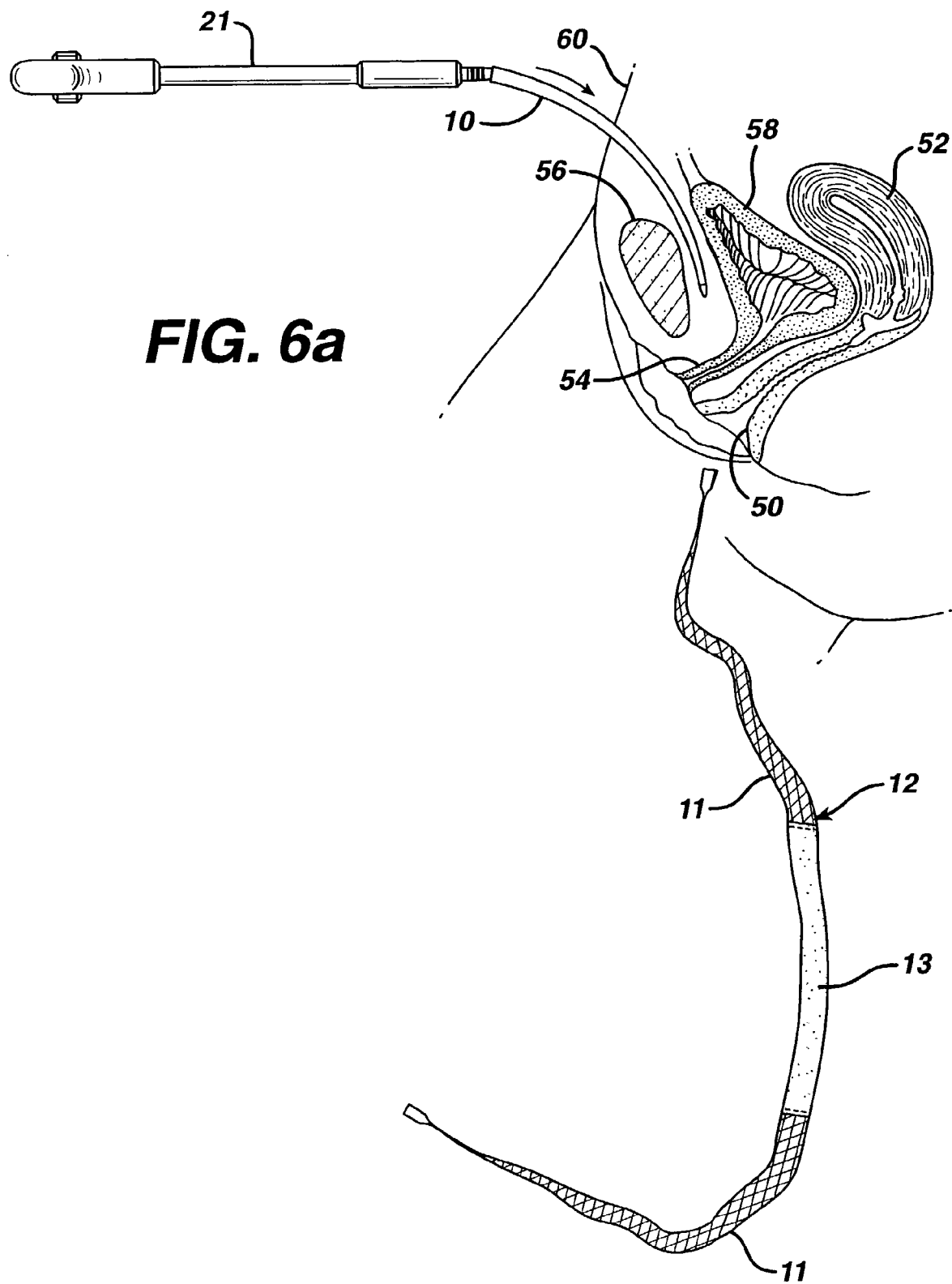
FIGS. 6a–h diagrammatically illustrate several surgical steps of a trans-abdominal method utilizing a single needle according to an alternate embodiment of the invention to treat SUI.
Figure 6B:
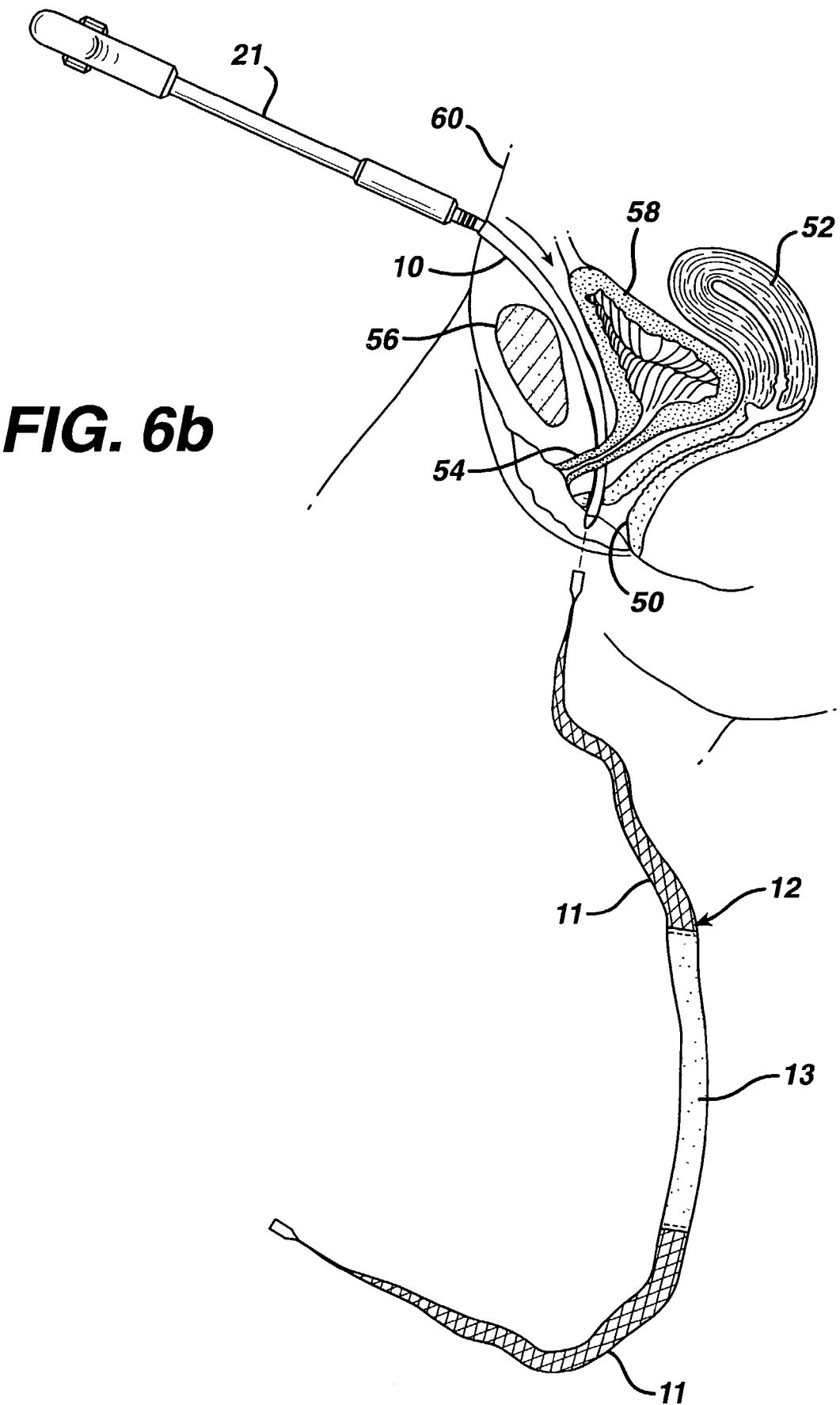
Figure 6C:
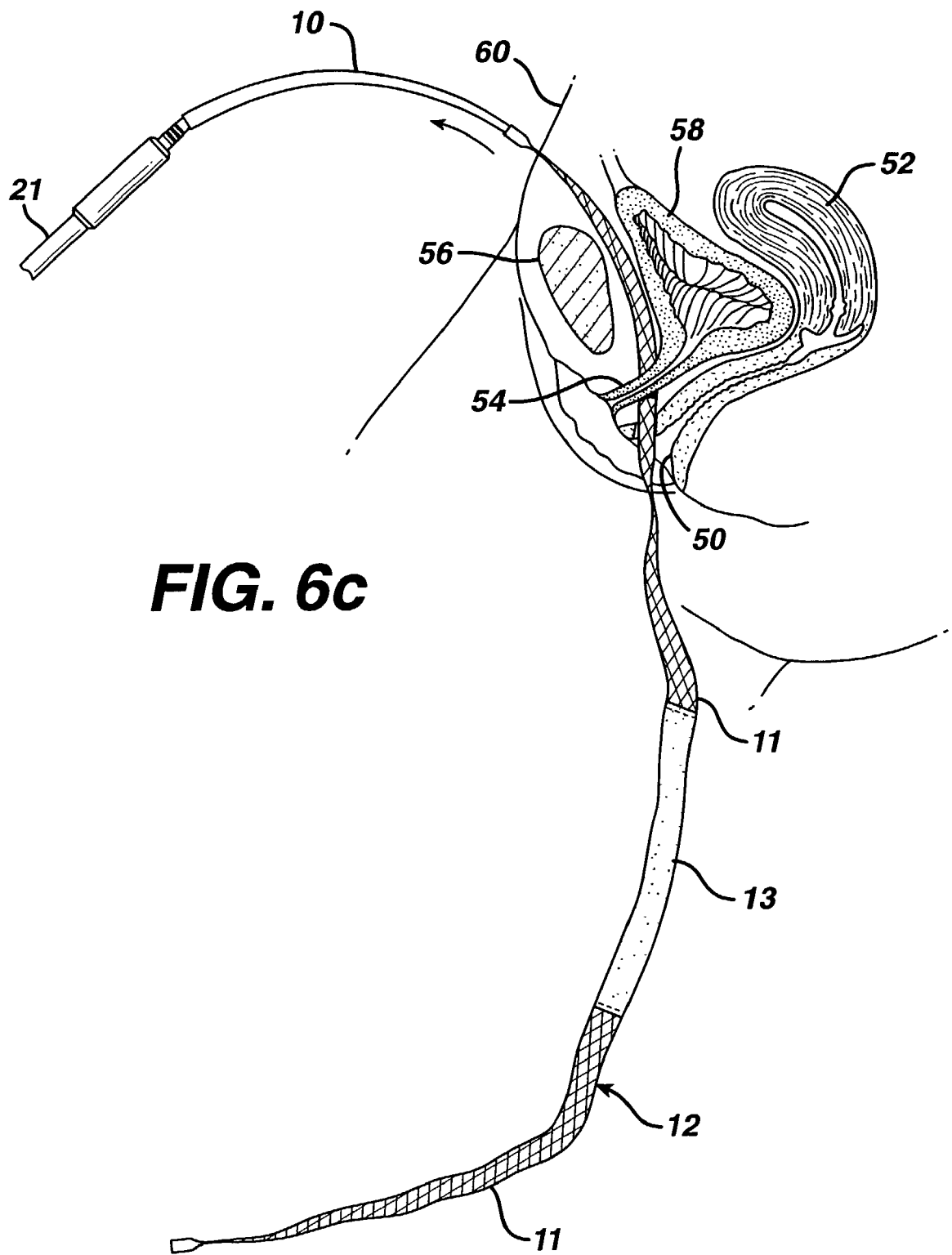
Figure 6D:
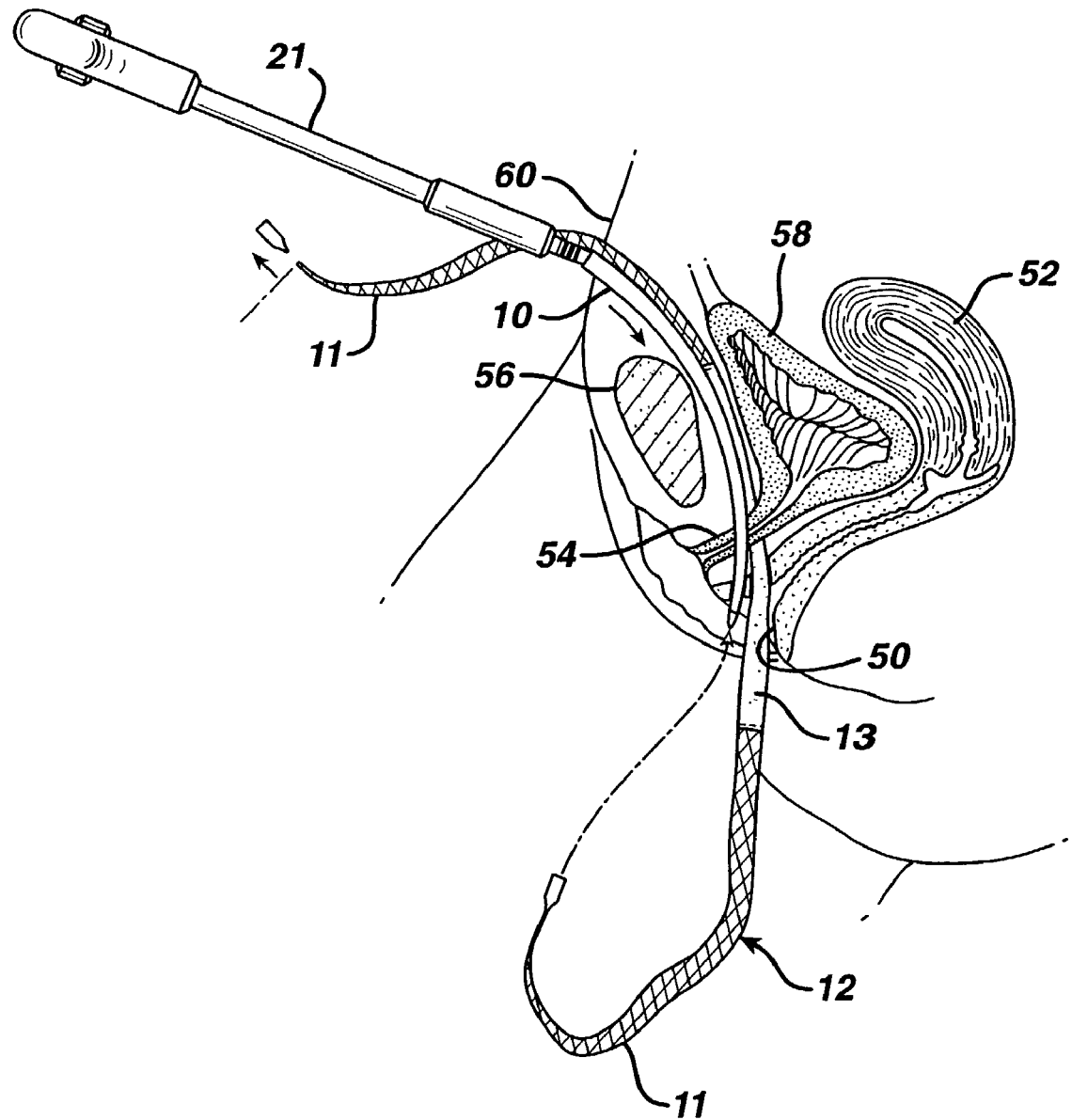
Figure 6E:
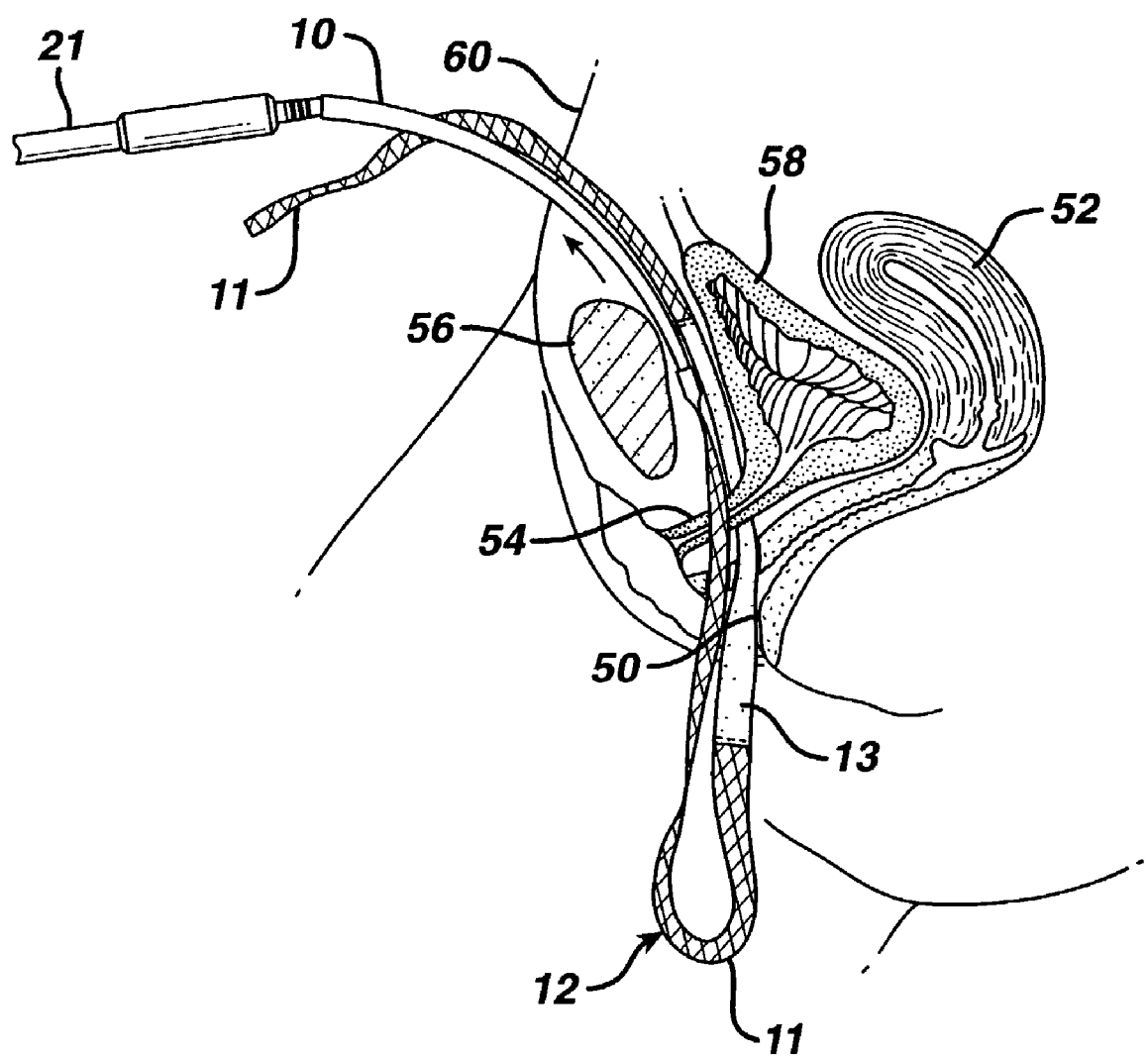
Figure 6F:
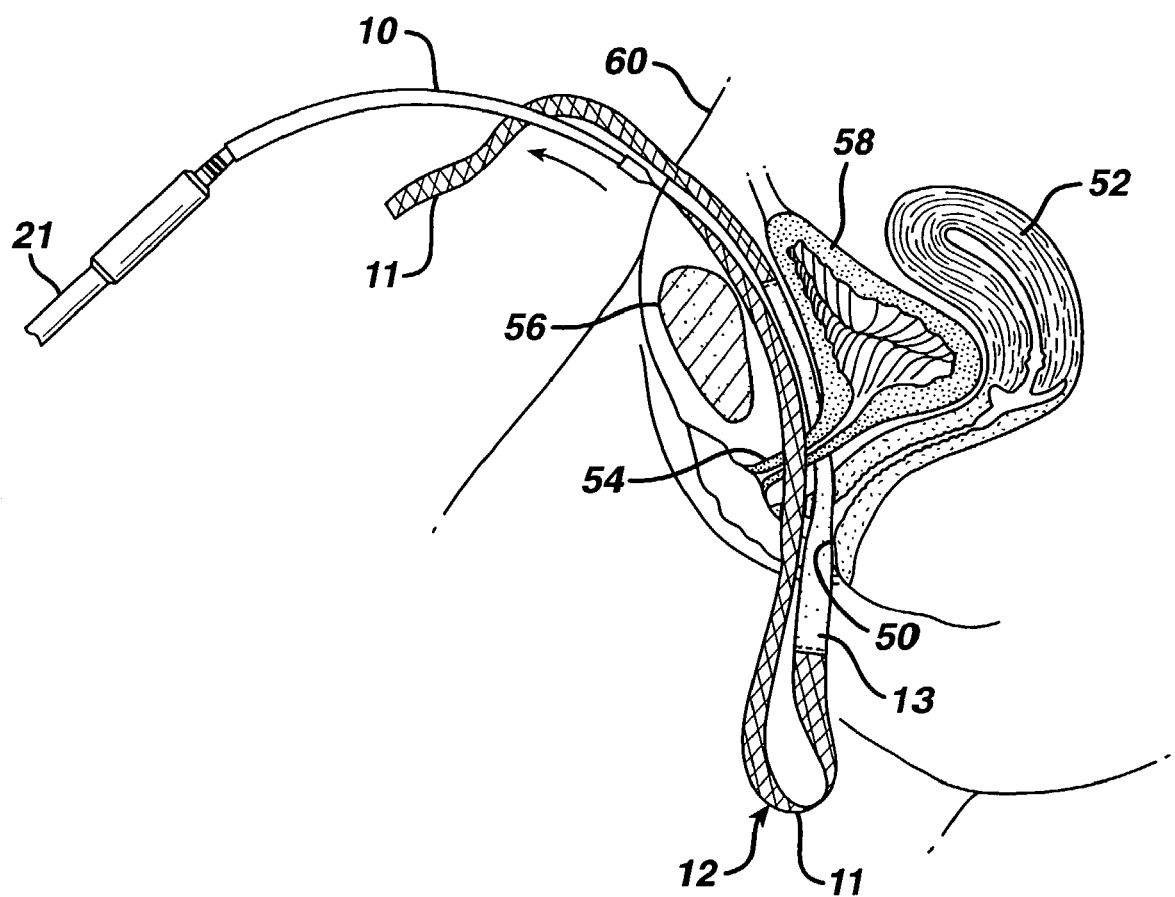
Figure 6G:
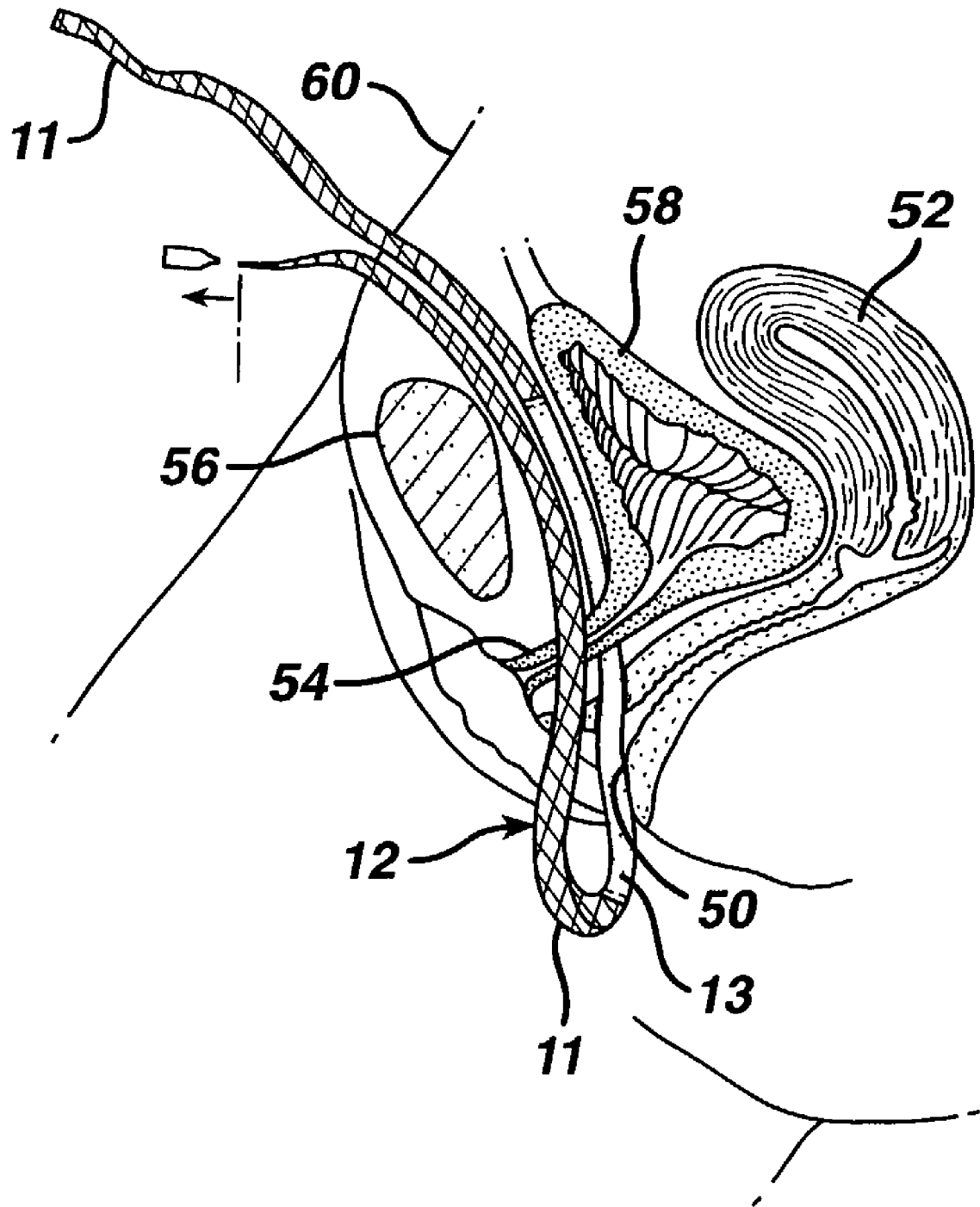
Figure 6H:
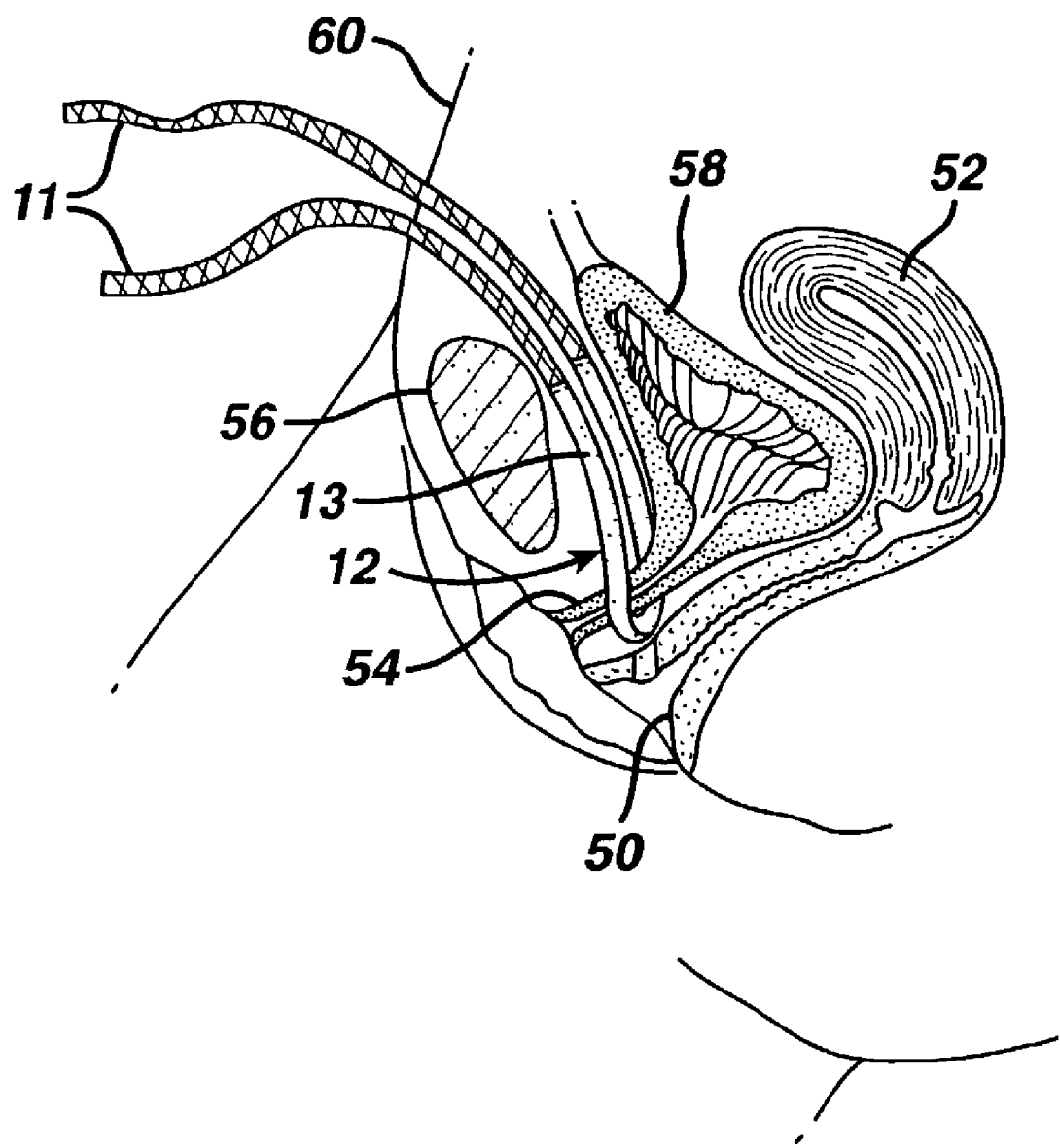

A needle 10 with coupling means at the distal end penetrates the abdominal wall 60, anterior to the pubic bone 56, FIG. 6a and follows the contour of the pubic bone 56 to one side of the urethra 54 and exits the body through an incision having been made in the anterior wall of the vagina 50, FIG. 6b. A first end of mesh 12 attaches to the distal end of needle 10 via coupling means. The surgeon then retracts needle 10 back through the pelvic cavity, following the same path created by needle 10, while at the same time causing mesh 12 to follow the needle, FIG. 4c. The needle 10 and mesh 12 pass through the vaginal wall and through the soft tissue on one side of the urethra 54. The needle and mesh then according to FIG. 4f being passed close to the back of the pubic bone 56, through additional layers of fat, muscle and fascia, and then out the abdominal wall 60 above the pubic bone 56.

Needle 10 disconnects from the first mesh end, and the surgeon repeats the same procedure, but this time passes the needle 10 on the opposite side of the urethra 54, FIGS. 6d–h, to complete the implantation of the mesh 12 between the mid urethra and vaginal wall.

Figure 7A:
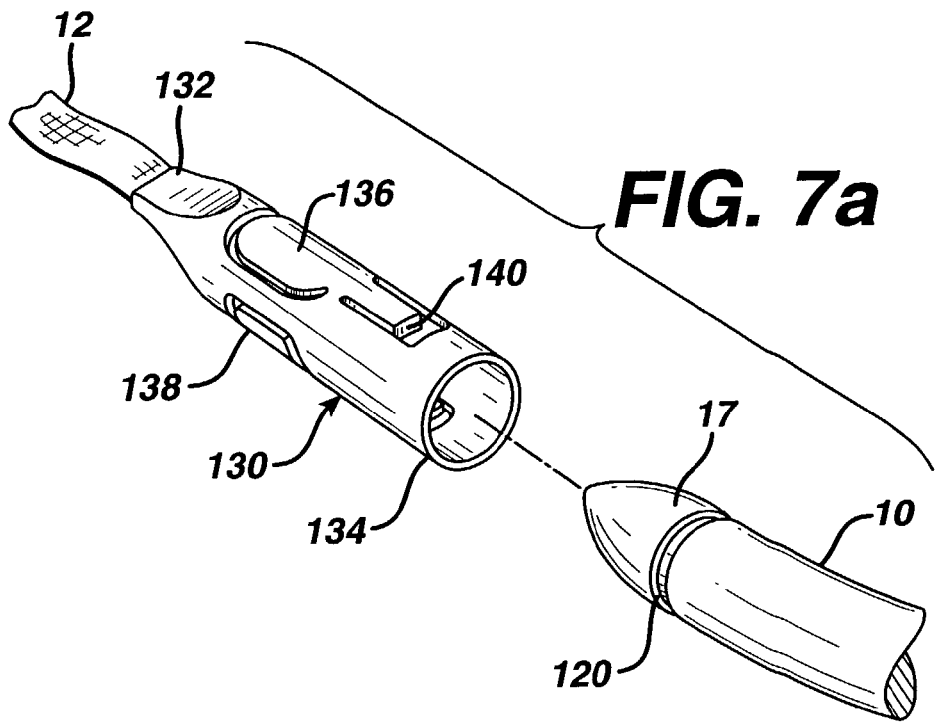
FIGS. 7a–g illustrate alternate embodiments of coupling the needle to the mesh.
Figure 7B:
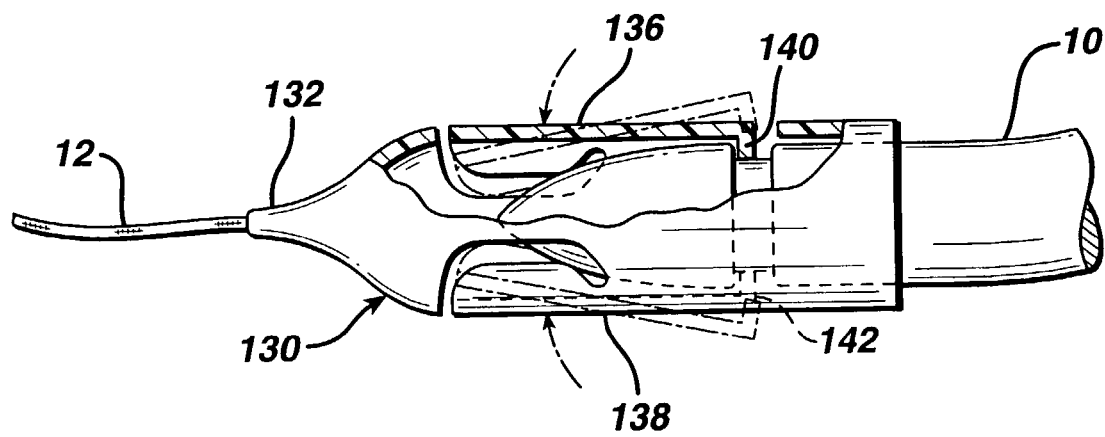

Referring to FIGS. 7a–g, alternate embodiments for connecting the needle 10 to the mesh 12 are disclosed. FIGS. 7a–b disclose a coupler 130 having a proximal end 132 configured to accept the mesh 12 and a distal end 134 for accepting the distal end 17 of needle 10. Distal end 17 comprises a contiguous groove 120 for detachably coupling with coupler 130. Coupler 130 further comprises two spring tabs 136 and 138, each with fingers 140 and 142 for engaging groove 120. Mesh 12 is preferably attached to the distal end 132 using a biocompatible glue or other appropriate mechanical fastening means. The surgeon may simply attach or detach needle 10 from coupler 130 by depressing spring tabs 136 and 138 forcing fingers 140 and 142 upward to allow distal end 17 to slide in or out of coupler 130. Fingers 140 and 142 engage groove 120 to hold needle 10 firmly in place within coupler 130.

Figure 7C:
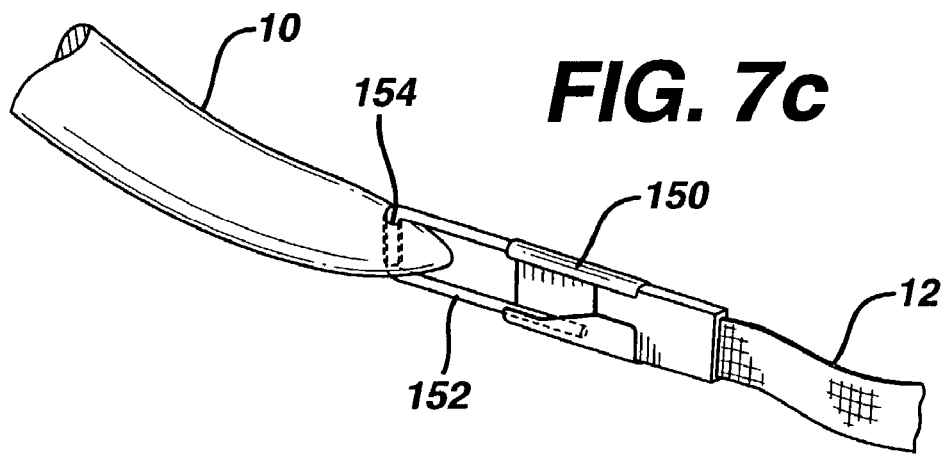
Figure 7D:
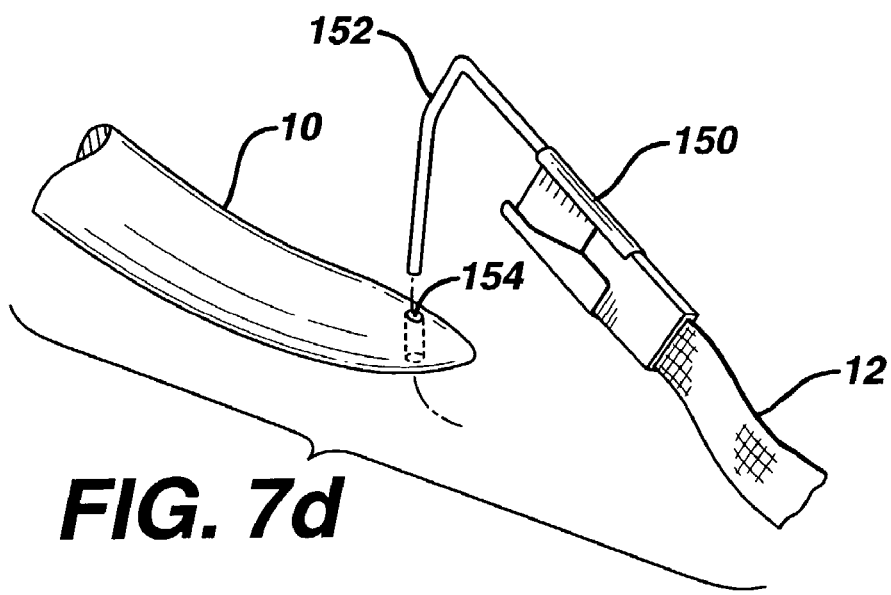
Figure 7E:
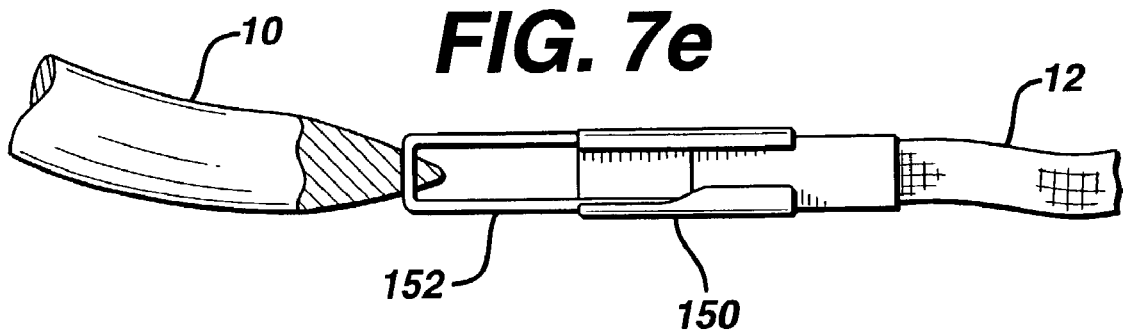

FIGS. 7c–e illustrate a coupling mechanism 150 similar in function to a safety pin. Spring arm 152 engages with a bore 154 at the distal end 17 of needle 10.

Figure 7F:
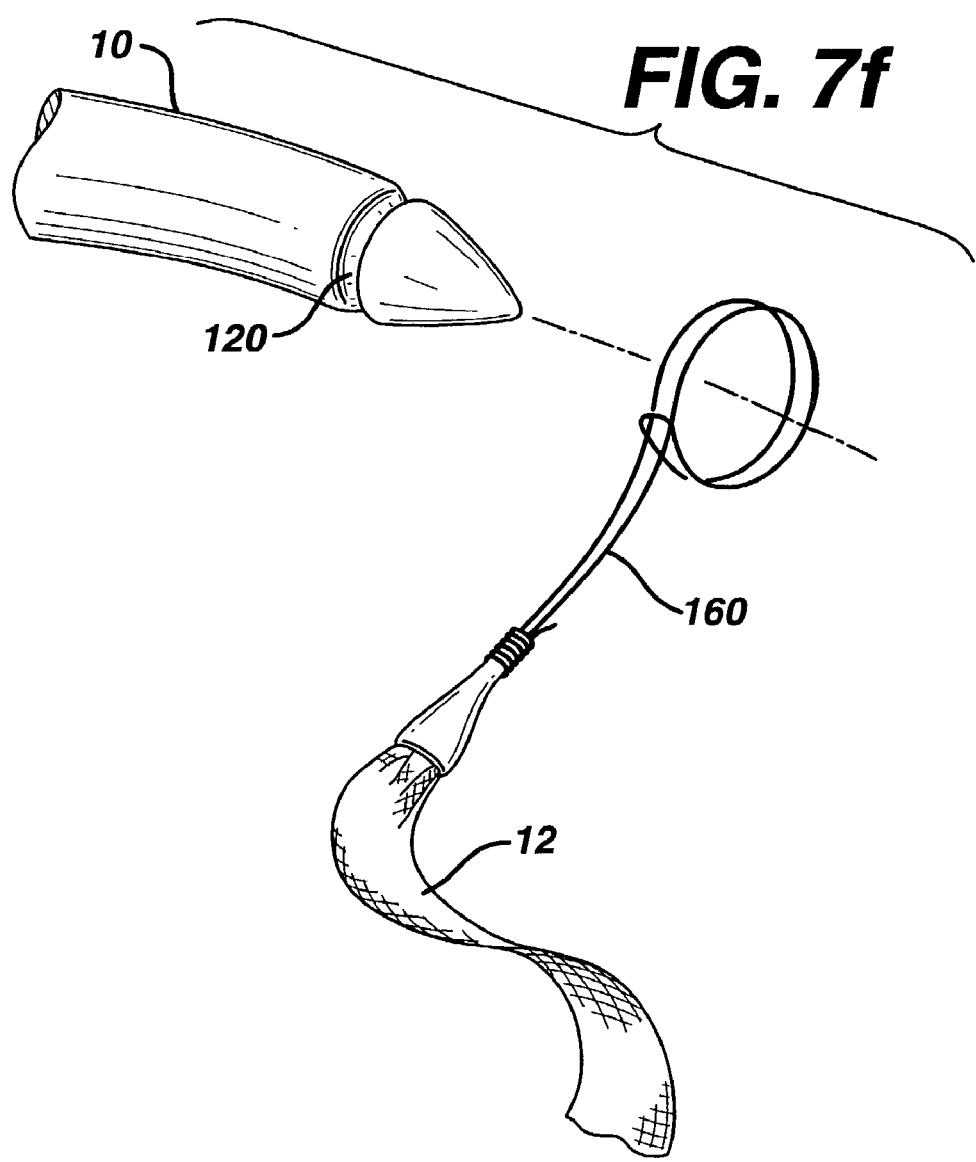
Figure 7G:
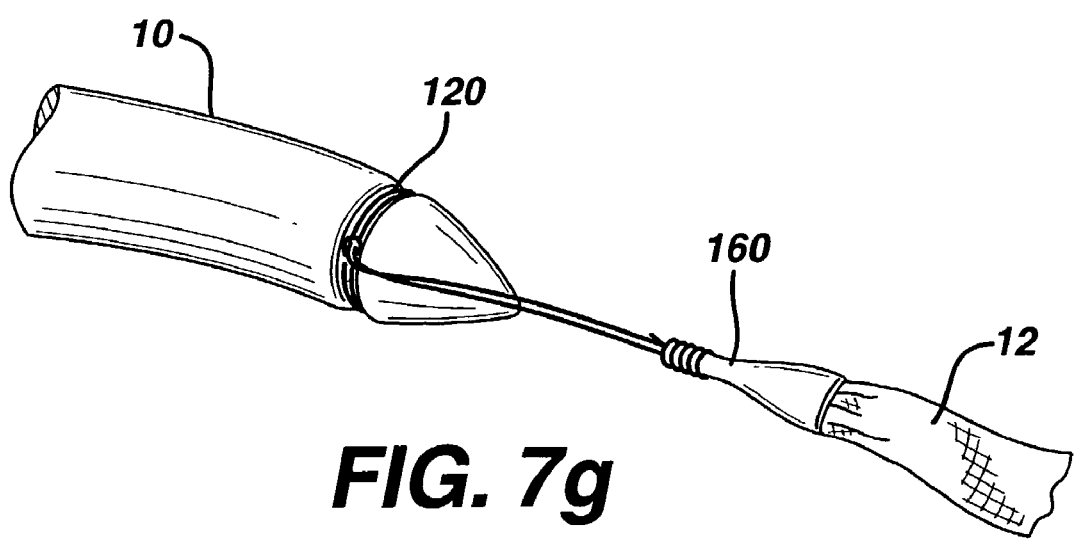
Figure 8A:
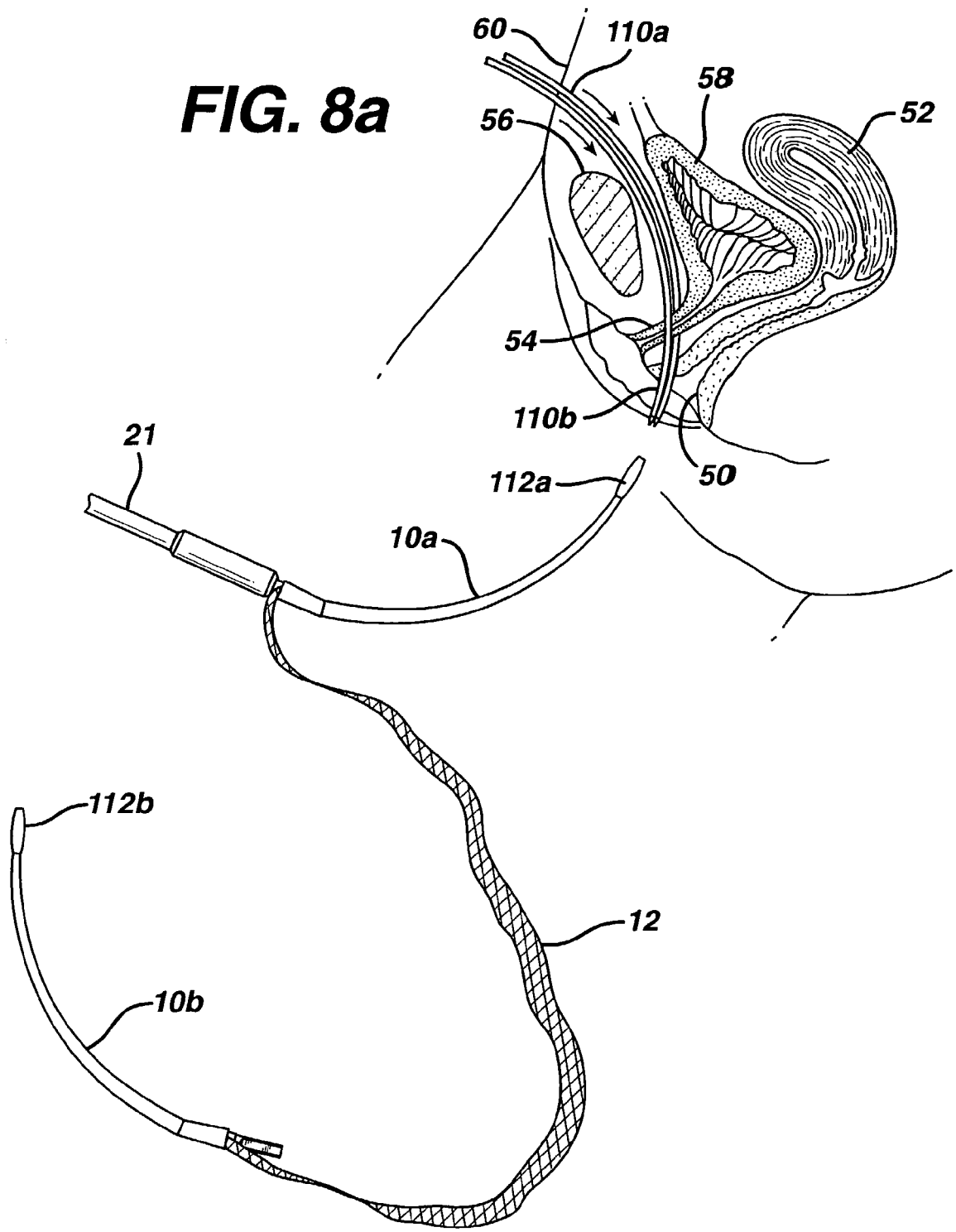
FIGS. 8a–i diagrammatically illustrate several surgical steps of a trans-abdominal method utilizing two needles and two guide needles according to the invention to treat SUI
Figure 8B:
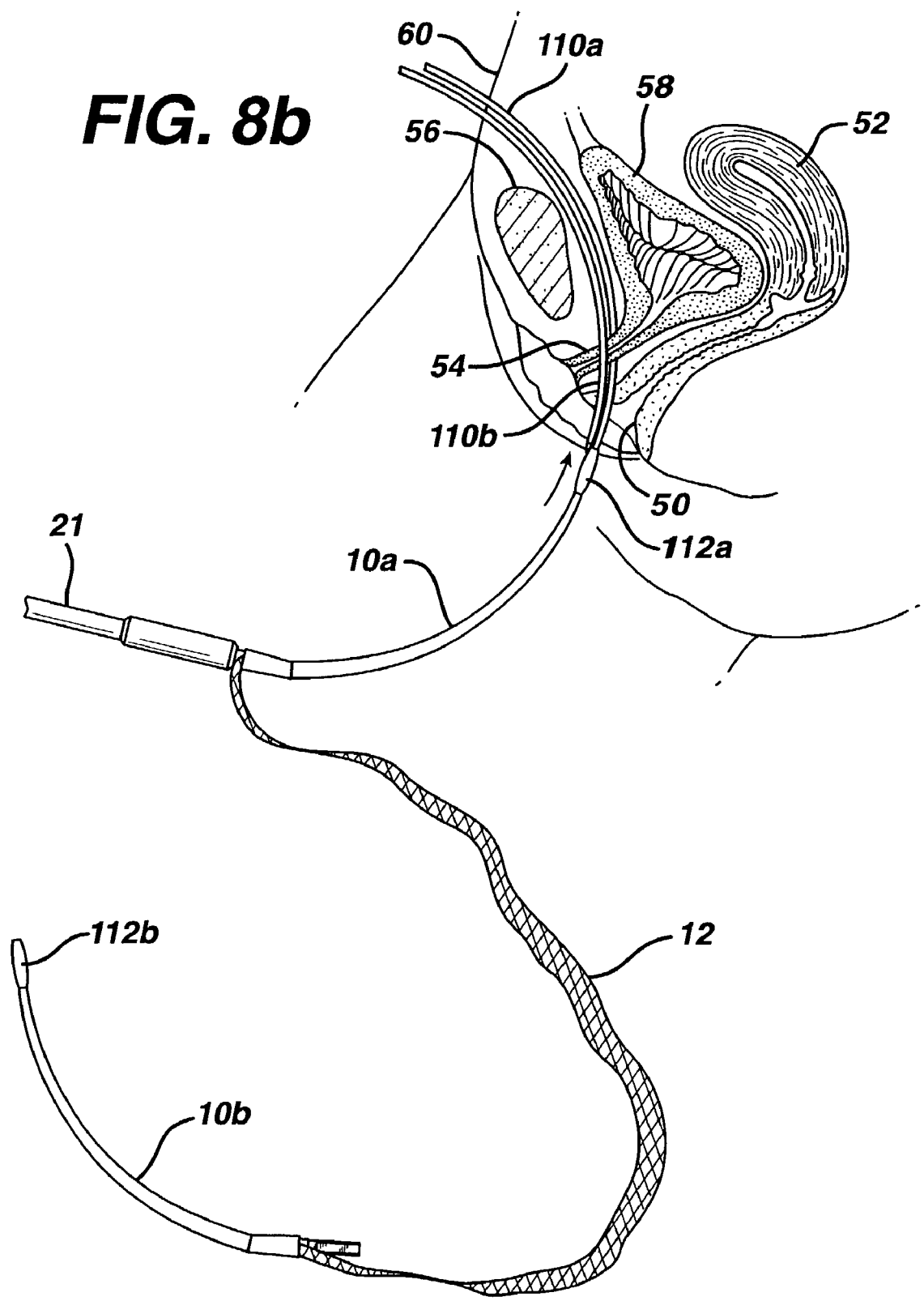
Figure 8C:
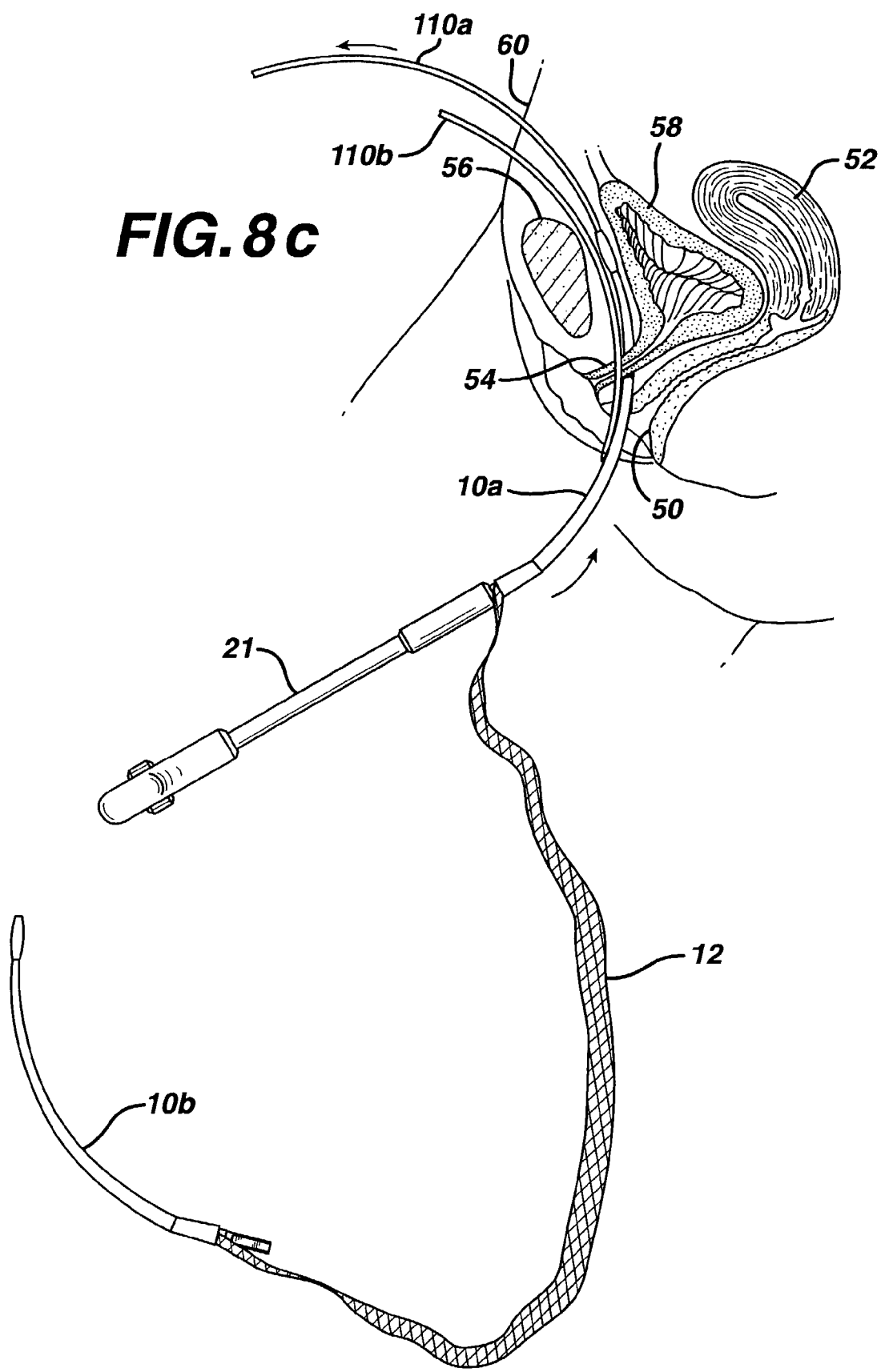
Figure 8D:
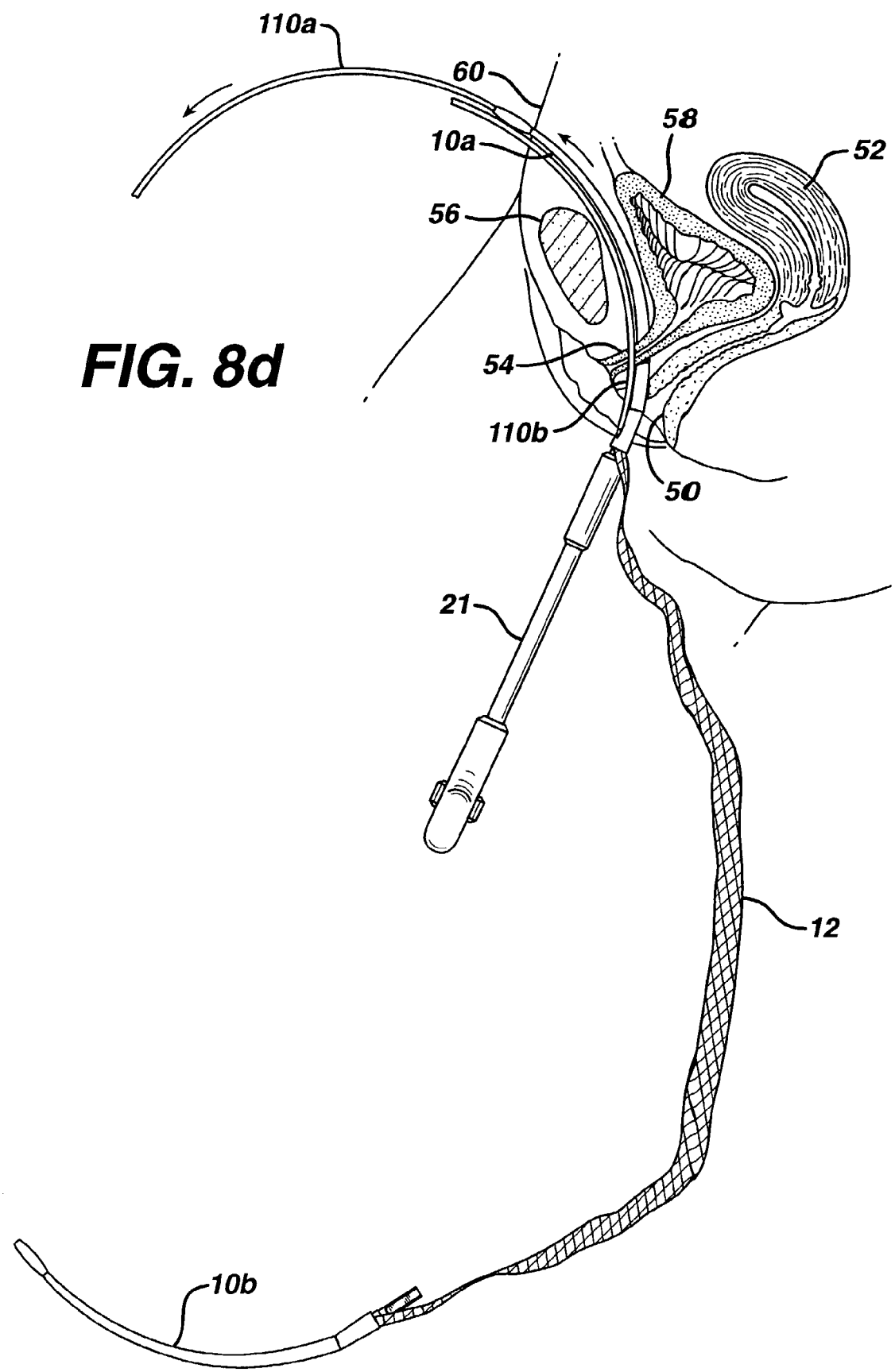
Figure 8E:
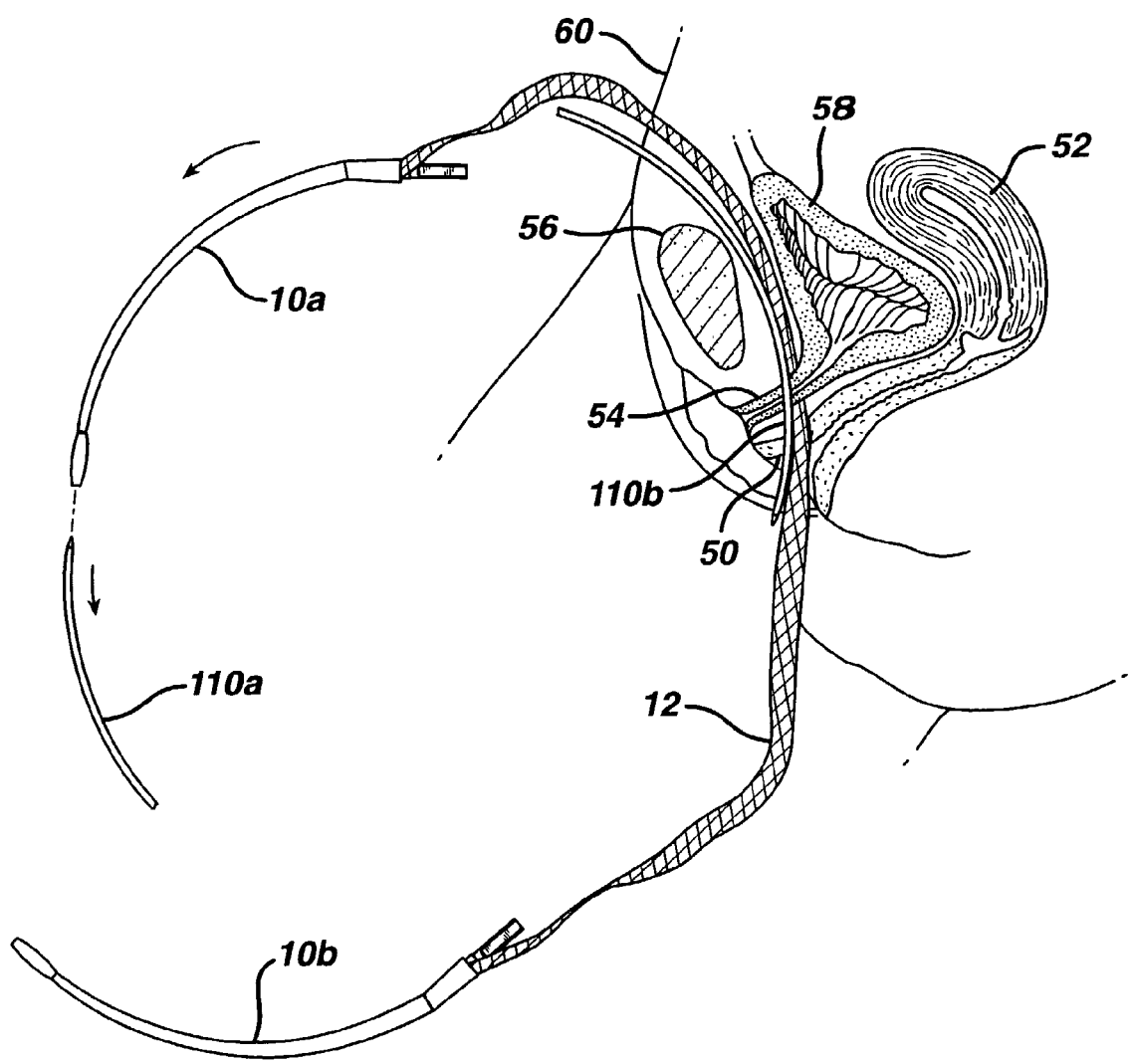
Figure 8F:
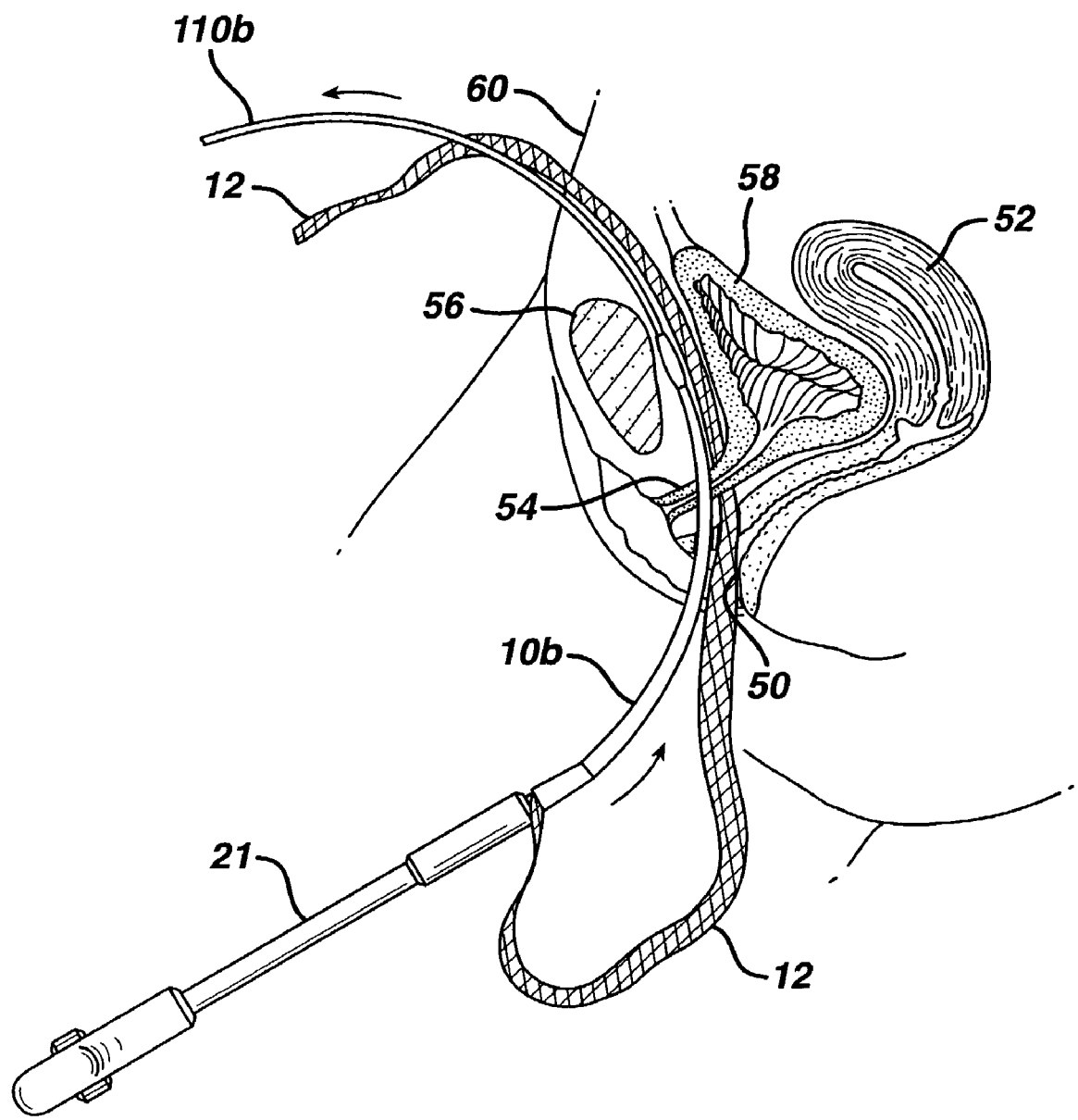
Figure 8G:
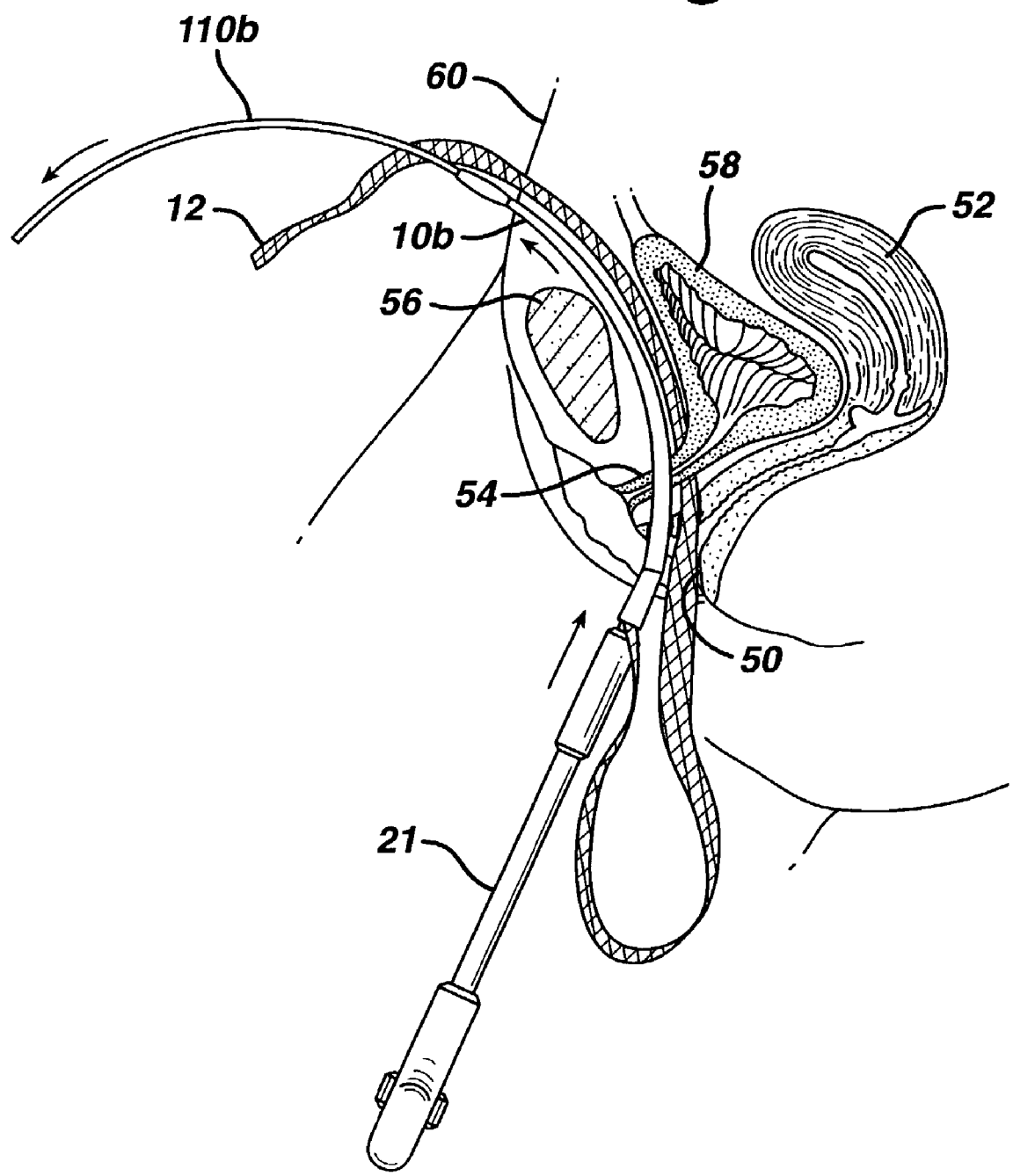
Figure 8H:
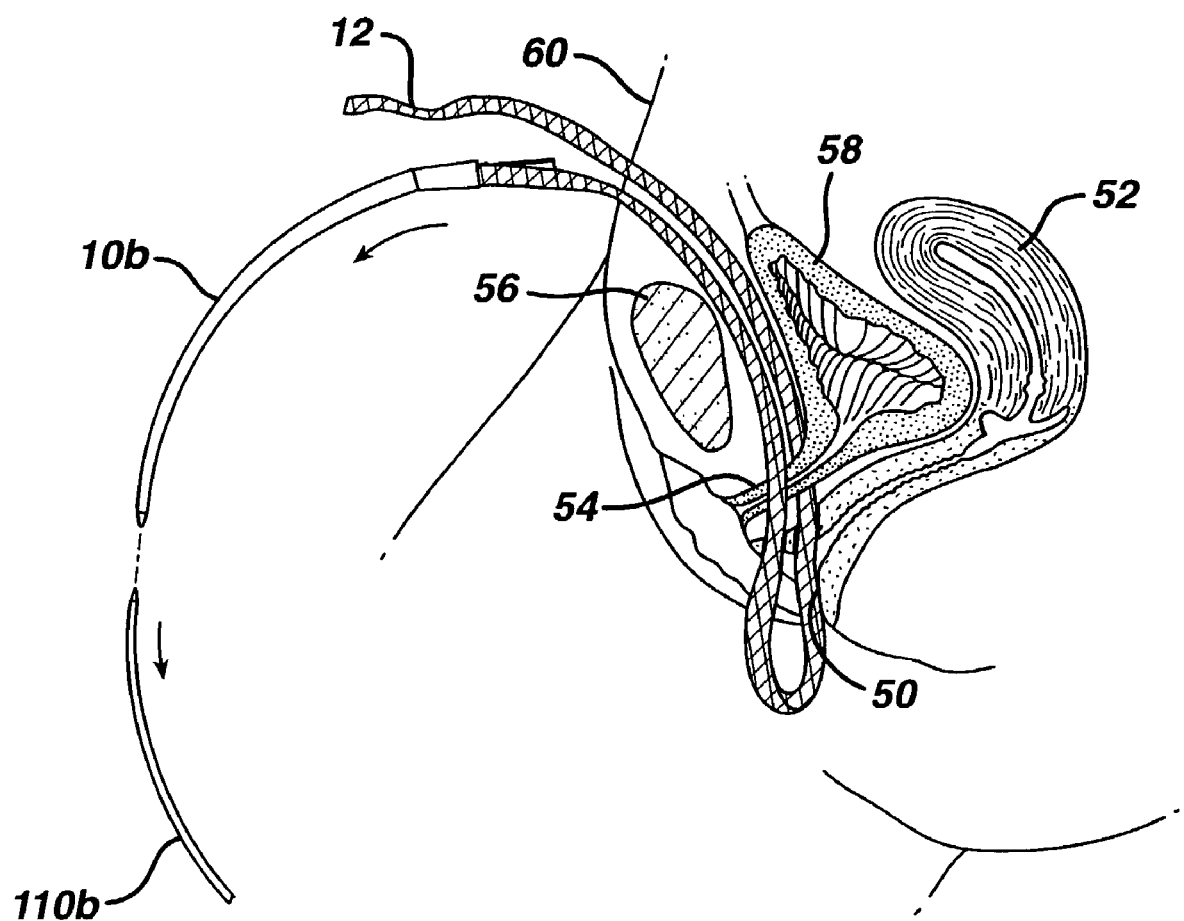
Figure 8I:
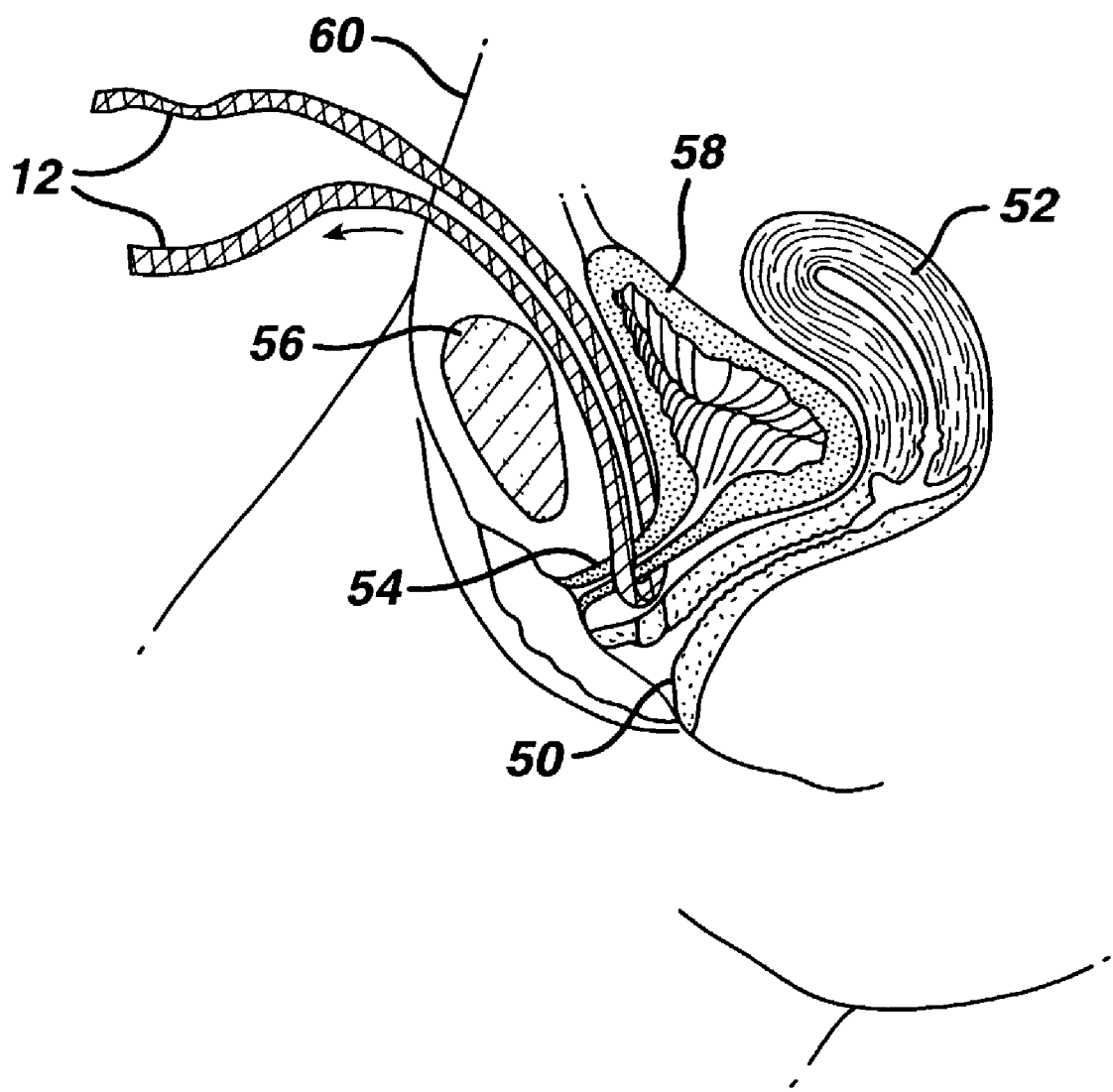

FIGS. 7f–g illustrate a loop coupling mechanism 160 attached to mesh 12 for engaging groove 120.

As would be appreciated by one skilled in the art, there exist multiple means for detachably connecting the mesh to the needle.

Since all procedures may be performed using a local anesthesia, the patient is able to provide feedback to the surgeon after mesh 12 is in place. Typically, the urinary bladder 58 is filled with a fluid, such as water, using a catheter and the patient is requested to cough. The surgeon is able to determine the operation of the urethra and may adjust the placement of the mesh 12, as necessary, by adjusting the ends of mesh 12 located at the outside of the abdomen 60, FIGS. 4h and 5h. After adjustments, the surplus mesh at the abdomen is cut off, and the ends of the mesh are secured within the abdomen and the abdomen is closed. Likewise, the incision at the vaginal wall is closed whereby the tissue flap seals the mesh between the urethra 54 and the wall of vagina 50.

Mesh 12 is left in the body and forms an artificial ligament attached to the abdominal wall that provides the support for the urethra as required in order to restore urinary continence to the patient.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. A surgical instrument assembly for treating female urinary stress incontinence comprising:
  a mesh for implanting into the lower abdomen of a female to provide support to the urethra;

a curved needle element having a distal end and a proximal end and defining in part a curved shaft, the proximal end being coupled to a first end of the mesh;

a curved needle guide having a proximal end and a distal end; and a coupling element for coupling the distal end of the needle element to the distal end of the needle guide.

2. The surgical instrument assembly according to claim 1, wherein the coupling element has a first bore therein in a first end and a second bore therein in a second end, wherein the first bore is dimensioned to receive the distal end of the needle element and the second bore is dimensioned to receive the distal end of the needle guide.

3. The surgical instrument assembly according to claim 2, wherein the coupling element is substantially elliptical in shape.

4. The surgical instrument assembly according to claim 2, wherein the coupling element is a tube element having a varying inner diameter.

5. The surgical instrument assembly according to claim 2, wherein the coupling element is a tube element having varying inner and outer diameters.

6. The surgical instrument assembly according to claim 2, wherein the first and second ends of the coupling element are tapered.

7. A surgical instrument assembly for treating female urinary stress incontinence comprising:

a mesh for implanting into the lower abdomen of a female to provide support to the urethra;

a curved needle element having a distal end and a proximal end and defining in part a curved shaft, the proximal end being coupled to a first end of the mesh; and a curved needle guide having a proximal end and a distal end;

wherein the distal end of the needle has a bore therein dimensioned to receive the distal end of the needle guide.

8. A surgical instrument assembly for treating female urinary stress incontinence comprising:

a mesh for implanting into the lower abdomen of a female to provide support to the urethra;

a curved needle element having a distal end and a proximal end and defining in part a curved shaft, the proximal end being coupled to a first end of the mesh; and a curved needle guide having a proximal end and a distal end, wherein the distal end has a bore therein dimensioned to receive the distal end of the needle element.

9. The surgical instrument assembly according to claim 8, wherein the distal end of the needle element further comprises a protruding element projecting outwardly therefrom, and the needle guide bore is dimensioned to receive therein the protruding element.

10. A surgical instrument assembly for treating female urinary stress incontinence comprising:

a curved needle element having a distal end and a proximal end and defining in part a curved shaft;

a mesh for implanting into the lower abdomen of a female to provide support to the urethra; and a connecting element coupled to a first end of the mesh and capable of being detachably coupled to the distal end of the needle element, wherein the connecting element has a first end and a second end, the first end being coupled to the mesh, and the second end further comprises an arm element projecting outwardly therefrom, and wherein the distal end of the needle element has a bore therein dimensioned to receive the arm element to thereby removably couple the mesh to the needle element.

11. The surgical instrument assembly according to claim 10, wherein the distal end of the needle element further comprises a circumferential groove therein, and wherein the connecting element further comprises a flexible loop element coupled thereto, wherein the flexible loop element is capable of engaging the circumferential groove to thereby removably coupled the mesh to the needle element.

12. The surgical instrument assembly according to claim 10, further comprising a second connecting element coupled to a second end of the mesh and capable of being detachably coupled to the distal end of the needle element.

13. A method for treating female urinary stress incontinence comprising:

passing a needle guide through a first path through the abdominal wall, along one side of the urethra, and through an anterior wall of the vagina;

attaching a first end of a coupling element to a distal end of the needle guide and a second end of the coupling element to a distal end of a first needle element, the first needle element being coupled to a first end of a mesh;

retracting the needle guide, the first needle element, and mesh back through the abdominal wall substantially via the first path;

uncoupling the needle guide from the coupling element;

passing the needle guide through a second path through the abdominal wall, along an opposite side of the urethra, and through the anterior wall of the vagina;

attaching a first end of a coupling element to a distal end of the needle guide, and a second end of the coupling element to a distal end of a second needle element, the second needle element being coupled to a second end of the mesh; and retracting the needle guide, second needle element, and mesh back through the abdominal wall substantially via the second path to thereby position the mesh between the urethra and vaginal wall to thereby provide support to the urethra.

14. The method according to claim 13, wherein the coupling element of the first and second attaching step is the same coupling element.

* * * * *